US012502413B2

(12) United States Patent
Cui et al.

(10) Patent No.: US 12,502,413 B2
(45) Date of Patent: Dec. 23, 2025

(54) ANTIBACTERIAL PHAGE, THERAPEUTIC COMPOSITION, BACTERICIDAL AGENT, FOOD, BACTERIA IDENTIFICATION KIT, THERAPEUTIC COMPOSITION MANUFACTURING METHOD, BACTERIA ELIMINATION METHOD, BACTERIA IDENTIFICATION METHOD, AND ANIMAL THERAPEUTIC METHOD

(71) Applicant: JICHI MEDICAL UNIVERSITY, Tokyo (JP)

(72) Inventors: Longzhu Cui, Shimotsuke (JP); Kotaro Kiga, Tsukuba (JP)

(73) Assignee: JICHI MEDICAL UNIVERSITY, Tokyo (JP)

( * ) Notice: Subject to any disclaimer, the term of this patent is extended or adjusted under 35 U.S.C. 154(b) by 1327 days.

(21) Appl. No.: 17/057,678

(22) PCT Filed: Apr. 19, 2019

(86) PCT No.: PCT/JP2019/016801
§ 371 (c)(1),
(2) Date: Nov. 22, 2020

(87) PCT Pub. No.: WO2019/225246
PCT Pub. Date: Nov. 28, 2019

(65) Prior Publication Data

US 2021/0205380 A1 Jul. 8, 2021

(30) Foreign Application Priority Data

May 22, 2018 (JP) ................................ 2018-097751

(51) Int. Cl.
*A61K 35/76* (2015.01)
*A23L 33/10* (2016.01)
(Continued)

(52) U.S. Cl.
CPC .............. *A61K 35/76* (2013.01); *A23L 33/10* (2016.08); *A61P 31/04* (2018.01); *C12N 15/113* (2013.01);
(Continued)

(58) Field of Classification Search
CPC .. C12N 15/86; C12N 15/113; C12N 15/1137; C12N 2795/14143; C12N 2795/14132;
(Continued)

(56) References Cited

U.S. PATENT DOCUMENTS

2016/0186147 A1 6/2016 Cady et al.
2017/0037414 A1 2/2017 Mikawa et al.

FOREIGN PATENT DOCUMENTS

JP 2017-513489 A 6/2017
JP 2017-537643 A 12/2017
(Continued)

OTHER PUBLICATIONS

East-Seletsky et al. RNA Targeting by Functionally Orthogonal Type VI-A CRISPR-Cas Enzymes. Molecular Cell (2017), 66, 373-383. (Year: 2017).*
(Continued)

*Primary Examiner* — Sean C. Barron
(74) *Attorney, Agent, or Firm* — Hawaii Patent Services; Nathaniel K. Fedde; Kenton N. Fedde

(57) ABSTRACT

Provided are antibacterial phages that selectively kill bacteria having a drug resistance gene or the like. Antibacterial phage for this includes CRISPR-Cas13a with a target sequence that recognizes a specific gene as a target. This target sequence is designed as a spacer sequence for crRNA of 14-28 bases. Specific genes are drug resistance genes and toxins. The drug resistance genes are included in bacterial genomes and/or plasmids having one or any combination of the group including: methicillin-resistant *Staphylococcus*
(Continued)

*aureus*, vancomycin-resistant *Staphylococcus aureus*, vancomycin-resistant enterococci, penicillin-resistant pneumococcus, multidrug-resistant *Pseudomonas aeruginosa*, multidrug-resistant *Pseudomonas aeruginosa*, carbapenem-resistant *Pseudomonas aeruginosa*, carbapenem-resistant cephalosporins, third-generation cephalosporin-resistant *Pseudomonas aeruginosa*, third-generation cephalosporin-resistant *E. coli*, and fluoroquinolone-resistant *E. coli*.

21 Claims, 23 Drawing Sheets

Specification includes a Sequence Listing.

(51) Int. Cl.
*A61P 31/04* (2006.01)
*C12N 15/113* (2010.01)
*C12N 15/86* (2006.01)
*C12Q 1/04* (2006.01)
*C12Q 1/18* (2006.01)

(52) U.S. Cl.
CPC .......... *C12N 15/1137* (2013.01); *C12N 15/86* (2013.01); *C12Q 1/04* (2013.01); *C12Q 1/18* (2013.01); *C12Y 301/00* (2013.01); *C12N 2310/20* (2017.05); *C12N 2320/32* (2013.01); *C12N 2795/14132* (2013.01); *C12N 2795/14141* (2013.01); *C12N 2795/14143* (2013.01); *G01N 2333/005* (2013.01); *Y02A 50/30* (2018.01)

(58) Field of Classification Search
CPC ...... C12N 2310/20; C12N 2795/14141; C12N 2320/32; A61K 35/76; C12Y 301/00; A61P 31/04; C12Q 1/04; C12Q 1/18; A23L 33/10; G01N 2333/005; Y02A 50/30
See application file for complete search history.

(56) References Cited

FOREIGN PATENT DOCUMENTS

| | | | | | |
|---|---|---|---|---|---|
| WO | 2014124226 | A1 | | 8/2014 | |
| WO | 2014204726 | A1 | | 12/2014 | |
| WO | 2015034872 | A2 | | 3/2015 | |
| WO | WO-2015159068 | A1 | * | 10/2015 | ............. A61K 35/76 |
| WO | 2016205276 | A1 | | 12/2016 | |
| WO | 2017066588 | A2 | | 4/2017 | |
| WO | 2017139505 | A2 | | 8/2017 | |
| WO | 2017173229 | A1 | | 10/2017 | |

OTHER PUBLICATIONS

Xue et al. Prediction of CRISPR sgRNA Activity Using a Deep Convolutional Neural Network. J. Chem. Inf. Model. (epub Nov. 2018), 59, 615-624. (Year: 2018).*

Shmakov S et al., "Discovery and Functional Characterization of Diverse Class 2 CRISPR-Cas Systems", Mol Cell, Nov. 5, 2015, 60(3), p. 385-397.

Abudayyeh OO et al., "C2c2 is a single-component programmable RNA-guided RNA-targeting CRISPR effector.", Science, Aug. 5, 2016, 353(6299), aaf5573.

Gootenberg JS et al., "Nucleic acid detection with CRISPR-Cas13a/C2c2.", Science, Apr. 28, 2017, 356(6336), p. 438-442.

Mahas, A. et al., "Harnessing CRISPR/Cas systems for Programmable transcriptional and post-transcriptional regulation", Biotechnol. Adv., Nov. 29, 2017, vol. 36, No. 1, pp. 295-310, in particular, abstract, section "3.3.4.", section "3.3.4.1.", fig. 4, section "4.2.", fig. 5G.

Bikard, D. et al., "Exploiting CRISPR-Cas nucleases to produce sequence-specific antimicrobials", Nat. Biotechnol., 2014, vol. 32, No. 11, pp. 1146-1150, in particular, abstract, p. 1149, left column, paragraph [0003].

Citorik, R. J. et al., "Sequence-specific antimicrobials using efficiently delivered RNA-guided nucleases", Nat. Biotechnol., 2014, vol. 32, No. 11, pp. 1141-1145, in particular, abstract.

Abudayyeh, O. O. et al., "C2c2 is a single-component programmable RNA-guided RNA-targeting CRISPR effector", Science, 2016, vol. 353, issue. 6299.

Park, J. Y. et al., "Genetic engineering of a temperate phage-based deliver system for CRISPR/Cas9 antimicrobials against *Staphylococcus aureus*", Scientific Reports, 2017, vol. 7, article No. 44929.

Bikard, D. et al., "Using CRISPR-Cas systems as antimicrobials", Curr. Opin. Microbiol., 2017, vol. 37, pp. 155-160.

Wessels HH, et al., Massively parallel Cas13 screens reveal principles for guide RNA design. Nat. Biotechnol., Jun. 2020;38(6):722-727. doi: 10.1038/s41587-020-0456-9.

Kiga K et al: "Development of CRISPR-Cas13a-based antimicrobials capable of sequence-specific killing of target bacteria", Nature Communications, vol. 11, No. 1, Dec. 1, 2020.

* cited by examiner

| EXPERIMENTAL ITEMS | 1 | 2 | 3 | 4 |
|---|---|---|---|---|
| ▪ *bla*$_{IMP-1}$ GENE | + | − | + | − |
| ▪ *bla*$_{IMP-1}$ SEQUENCE RECOGNIZED BY CRISPR | − | − | + | + |
| ▪ CRISPR-Cas13a | + | + | + | + |

FIG.2A

BACTERIAL CULTURE SOLUTION AFTER 4 HOURS AND 8 HOURS OF ACTION OF CRISPR-Cas13a $bla_{IMP-1}$ TARGETED SYNTHETIC PHAGE SELECTIVELY KILL E. COLI EXPRESSING $bla_{IMP-1}$

SEQUENCE LISTING

```
<160> NUMBER OF SEQ ID NOS: 52

<210> SEQ ID NO 1
<211> LENGTH: 31
<212> TYPE: DNA
<213> ORGANISM: Escherichia coli

<400> SEQUENCE: 1

cggtctgggt accttcgtac ggacgacctt c                                    31


<210> SEQ ID NO 2
<211> LENGTH: 28
<212> TYPE: DNA
<213> ORGANISM: Escherichia coli

<400> SEQUENCE: 2

aaaacggcaa cactcgccac aagaacaa                                        28


<210> SEQ ID NO 3
<211> LENGTH: 28
<212> TYPE: DNA
<213> ORGANISM: Escherichia coli

<400> SEQUENCE: 3

cggatttata atcggcaaat tgcgcttt                                        28


<210> SEQ ID NO 4
```

<211> LENGTH: 28
<212> TYPE: DNA
<213> ORGANISM: Escherichia coli

<400> SEQUENCE: 4
ccattggcgt gatgccagtt tgcttatc 28

<210> SEQ ID NO 5
<211> LENGTH: 28
<212> TYPE: DNA
<213> ORGANISM: Escherichia coli

<400> SEQUENCE: 5
ccaccaaacc catcagcaca aaaggatt 28

<210> SEQ ID NO 6
<211> LENGTH: 28
<212> TYPE: DNA
<213> ORGANISM: Escherichia coli

<400> SEQUENCE: 6
ctgatttata atcaaaatac tgcgtggc 28

<210> SEQ ID NO 7
<211> LENGTH: 28
<212> TYPE: DNA
<213> ORGANISM: Escherichia coli

<400> SEQUENCE: 7
gcagttggct tgaatgtcgt attatttg 28

<210> SEQ ID NO 8
<211> LENGTH: 28
<212> TYPE: DNA
<213> ORGANISM: Escherichia coli

<400> SEQUENCE: 8
caaaatacag tgccaaaaag aacataag 28

<210> SEQ ID NO 9
<211> LENGTH: 28
<212> TYPE: DNA
<213> ORGANISM: Escherichia coli

<400> SEQUENCE: 9
ggtgatcctt tggttcgatt tcgatgtt 28

<210> SEQ ID NO 10
<211> LENGTH: 28
<212> TYPE: DNA
<213> ORGANISM: Escherichia coli

<400> SEQUENCE: 10
gtaaatccag gtgacatcca cacctgca 28

<210> SEQ ID NO 11
<211> LENGTH: 28
<212> TYPE: DNA
<213> ORGANISM: Escherichia coli

<400> SEQUENCE: 11
gcaacataaa acaacgcagt gatgaaag 28

<210> SEQ ID NO 12
<211> LENGTH: 28
<212> TYPE: DNA
<213> ORGANISM: Escherichia coli

<400> SEQUENCE: 12
gatcactctt caaatctatc gtgagatt 28

<210> SEQ ID NO 13
<211> LENGTH: 28
<212> TYPE: DNA
<213> ORGANISM: Escherichia coli

<400> SEQUENCE: 13
ctaaagtcat tagataccca agccagca 28

<210> SEQ ID NO 14
<211> LENGTH: 28
<212> TYPE: DNA
<213> ORGANISM: Escherichia coli

<400> SEQUENCE: 14
ctgatgaaca gagtcaaaaa ttcagtgc 28

<210> SEQ ID NO 15
<211> LENGTH: 28
<212> TYPE: DNA
<213> ORGANISM: Escherichia coli

<400> SEQUENCE: 15
gatggcctgc cgaagacagg ttttcaaa 28

<210> SEQ ID NO 16
<211> LENGTH: 28
<212> TYPE: DNA
<213> ORGANISM: Escherichia coli

<400> SEQUENCE: 16
cataaacctg actcgactgc caccagat 28

<210> SEQ ID NO 17
<211> LENGTH: 28
<212> TYPE: DNA
<213> ORGANISM: Escherichia coli

<400> SEQUENCE: 17
ttaacttctt caaacgaagt atgaacat 28

<210> SEQ ID NO 18
<211> LENGTH: 28
<212> TYPE: DNA
<213> ORGANISM: Escherichia coli

<400> SEQUENCE: 18
ccactctatt ccgcccgtgc tgtcgcta 28

<210> SEQ ID NO 19
<211> LENGTH: 28
<212> TYPE: DNA
<213> ORGANISM: Escherichia coli

<400> SEQUENCE: 19
aattaagcca ctctattccg cccgtgct 28

<210> SEQ ID NO 20
<211> LENGTH: 28
<212> TYPE: DNA
<213> ORGANISM: Escherichia coli

<400> SEQUENCE: 20
agaattaagc cactctattc cgcccgtg 28

<210> SEQ ID NO 21
<211> LENGTH: 28
<212> TYPE: DNA
<213> ORGANISM: Escherichia coli

<400> SEQUENCE: 21
ttaattcaga tgcatacgtg gggataga 28

<210> SEQ ID NO 22
<211> LENGTH: 28
<212> TYPE: DNA
<213> ORGANISM: Escherichia coli

<400> SEQUENCE: 22
ttcatttgtt aattcagatg catacgtg 28

<210> SEQ ID NO 23
<211> LENGTH: 28
<212> TYPE: DNA
<213> ORGANISM: Escherichia coli

<400> SEQUENCE: 23
ggcctggata aaaaacttca attttatt 28

<210> SEQ ID NO 24
<211> LENGTH: 28
<212> TYPE: DNA
<213> ORGANISM: Escherichia coli

<400> SEQUENCE: 24
acttggaaca accagttttg ccttacca 28

<210> SEQ ID NO 25
<211> LENGTH: 28
<212> TYPE: DNA
<213> ORGANISM: Escherichia coli

<400> SEQUENCE: 25
atcgccaaac cgttggtcgc cagtttcc 28

<210> SEQ ID NO 26
<211> LENGTH: 28
<212> TYPE: DNA
<213> ORGANISM: Escherichia coli

<400> SEQUENCE: 26
acaacgcatt ggcataagtc gcaatccc 28

<210> SEQ ID NO 27
<211> LENGTH: 28
<212> TYPE: DNA
<213> ORGANISM: Escherichia coli

<400> SEQUENCE: 27
aatggctcat cacgatcatg ctggcctt 28

<210> SEQ ID NO 28
<211> LENGTH: 28
<212> TYPE: DNA
<213> ORGANISM: Escherichia coli

<400> SEQUENCE: 28
attgggaatt ttaaaggtag atgcgggt 28

<210> SEQ ID NO 29
<211> LENGTH: 28
<212> TYPE: DNA
<213> ORGANISM: Escherichia coli

<400> SEQUENCE: 29
caatttggcg ggcaaattct tgataaac 28

<210> SEQ ID NO 30
<211> LENGTH: 28
<212> TYPE: DNA
<213> ORGANISM: Escherichia coli

<400> SEQUENCE: 30
gccgaaattc gaataccacc gtcgagcc 28

<210> SEQ ID NO 31
<211> LENGTH: 28
<212> TYPE: DNA
<213> ORGANISM: Escherichia coli

<400> SEQUENCE: 31
gtcagcgcgg tggcagaaaa gccagcca 28

<210> SEQ ID NO 32
<211> LENGTH: 28
<212> TYPE: DNA
<213> ORGANISM: Escherichia coli

<400> SEQUENCE: 32
cctgctgctg gctgcgagcc agcacagc 28

<210> SEQ ID NO 33
<211> LENGTH: 28
<212> TYPE: DNA
<213> ORGANISM: Escherichia coli

<400> SEQUENCE: 33
cccagtgggc cagacgacgg catagtca 28

<210> SEQ ID NO 34
<211> LENGTH: 28
<212> TYPE: DNA
<213> ORGANISM: Escherichia coli

<400> SEQUENCE: 34
ctgtatcaat caaaagcaac tcatcacc 28

<210> SEQ ID NO 35
<211> LENGTH: 28
<212> TYPE: DNA
<213> ORGANISM: Escherichia coli

<400> SEQUENCE: 35
ccgacgcggt cgtcatgaaa gtgcgtgg 28

<210> SEQ ID NO 36
<211> LENGTH: 28
<212> TYPE: DNA
<213> ORGANISM: Escherichia coli

<400> SEQUENCE: 36
tcggtcgaat gcgcagcacc aggataga 28

<210> SEQ ID NO 37
<211> LENGTH: 28
<212> TYPE: DNA
<213> ORGANISM: Escherichia coli

<400> SEQUENCE: 37
gactttggcc aagcttctat atttgcgt 28

<210> SEQ ID NO 38
<211> LENGTH: 28
<212> TYPE: DNA
<213> ORGANISM: Escherichia coli

<400> SEQUENCE: 38
gcggactttg gccaagcttc tatatttg 28

<210> SEQ ID NO 39
<211> LENGTH: 28
<212> TYPE: DNA
<213> ORGANISM: Escherichia coli

<400> SEQUENCE: 39
ttttgatggt tttttacttt cgtttaac 28

<210> SEQ ID NO 40
<211> LENGTH: 28
<212> TYPE: DNA
<213> ORGANISM: Escherichia coli

<400> SEQUENCE: 40
actttggcca agcttctata tttgcgtc 28

<210> SEQ ID NO 41
<211> LENGTH: 28
<212> TYPE: DNA
<213> ORGANISM: Escherichia coli

<400> SEQUENCE: 41
tggcttgaac cttaccgtct tttttaag 28

<210> SEQ ID NO 42
<211> LENGTH: 28
<212> TYPE: DNA
<213> ORGANISM: Escherichia coli

<400> SEQUENCE: 42
cggactttgg ccaagcttct atatttgc 28

<210> SEQ ID NO 43
<211> LENGTH: 28
<212> TYPE: DNA
<213> ORGANISM: Escherichia coli

<400> SEQUENCE: 43
tatctttagc cgtaaatgga gtgtcaat 28

<210> SEQ ID NO 44
<211> LENGTH: 28
<212> TYPE: DNA
<213> ORGANISM: Escherichia coli

<400> SEQUENCE: 44
tgctgtcgct atgaaaatga gaggaaat 28

<210> SEQ ID NO 45
<211> LENGTH: 28
<212> TYPE: DNA
<213> ORGANISM: Escherichia coli

<400> SEQUENCE: 45
tttcaagagt gatgcgtctc caacttca 28

<210> SEQ ID NO 46
<211> LENGTH: 28
<212> TYPE: DNA
<213> ORGANISM: Escherichia coli

<400> SEQUENCE: 46
caaaacaaaa atataaagaa tacagata 28

<210> SEQ ID NO 47
<211> LENGTH: 28
<212> TYPE: DNA
<213> ORGANISM: Escherichia coli

<400> SEQUENCE: 47
aacaaccagt tttgccttac catatttg 28

<210> SEQ ID NO 48
<211> LENGTH: 28
<212> TYPE: DNA
<213> ORGANISM: Escherichia coli

<400> SEQUENCE: 48
gttttgatgg ttttttactt tcgtttaa 28

<210> SEQ ID NO 49
<211> LENGTH: 28
<212> TYPE: DNA
<213> ORGANISM: Escherichia coli

<400> SEQUENCE: 49
tgactaactt ttcagtatct ttagccgt 28

<210> SEQ ID NO 50
<211> LENGTH: 28
<212> TYPE: DNA
<213> ORGANISM: Escherichia coli

<400> SEQUENCE: 50
gtcatggcat ttccactaaa ctccatta 28

<210> SEQ ID NO 51
<211> LENGTH: 28
<212> TYPE: DNA
<213> ORGANISM: Escherichia coli -continued

<400> SEQUENCE: 51
gtcattgtat taccactgaa ctccatta 28

<210> SEQ ID NO 52
<211> LENGTH: 28
<212> TYPE: DNA
<213> ORGANISM: Escherichia coli

<400> SEQUENCE: 52
attttaaatt ttcaatatgt atgctttg 28

ANTIBACTERIAL PHAGE, THERAPEUTIC COMPOSITION, BACTERICIDAL AGENT, FOOD, BACTERIA IDENTIFICATION KIT, THERAPEUTIC COMPOSITION MANUFACTURING METHOD, BACTERIA ELIMINATION METHOD, BACTERIA IDENTIFICATION METHOD, AND ANIMAL THERAPEUTIC METHOD

SEQUENCE LISTING

A sequence listing text file having the following identifying information is hereby incorporated by reference. Name: "sequence_15_Mar_2021.txt"; Date of creation: 15 Mar. 2021; Size: 8,145 bytes.

TECHNICAL FIELD

The present invention particularly relates to antibacterial phage, therapeutic composition, bactericidal agent, food, identification bacteria kit, therapeutic composition manufacturing method, bacteria elimination method, bacteria identification method, and animal therapeutic method.

BACKGROUND ART

In recent years, a technique called genome editing that modifies a target DNA by using a site-specific nuclease has attracted attention. For example, Patent Document 1 describes a technique for genome editing by using CRISPR (Clustered Regularly Interspaced Short Palindromic Repeats)/Cas9 (Crispr associated protein 9). In CRISPR/Cas9, a guide RNA including a sequence complementary to the target site of DNA and Cas9 nuclease are injected into the cell. Then, the guide RNA specifically binds to the target site. Then, the Cas9 protein binds and cleaves the DNA so as to cover the guide RNA and the DNA.

On the other hand, in recent years, the emergence of drug resistant bacteria that antibacterial drugs do not work and their rapid spread have become problems. In other words, since drug resistant bacteria appear at a speed far faster than the development of antibacterial drugs, bacterial infections have become a global problem that threatens human health again.

Here, conventionally, phage therapy, which is an antibacterial treatment method by using a bacteriophage (hereinafter just referred to as "phage"), has been known. The phage therapy is a therapeutic method that uses the lytic activity of a phage, which is a virus that infects bacteria, to kill them. It was attempted with the discovery of phages in 1915 and is still being applied clinically in some areas of Eastern Europe. The conventional phage have a lower bactericidal efficacy than antibacterial agents, and therefore, it has limitations as therapeutic products for bacterial infections.

CITATION LIST

Patent Literature

[Patent Document 1] PCT Publication No. 2014/204726

Non-Patent Literature

[Non-Patent Document 1] Shmakov, S, et al., "Discovery and Functional Characterization of Diverse Class 2 CRISPR-Cas Systems", Mol. Cell, 2015 Nov. 5, 60 (3), p. 385-397

[Non-Patent Document 2] Abudayyeh, 00, et al., "C2c2 is a single-component programmable RNA-guided RNA-targeting CRISPR effector.", Science, 2016 Aug. 5, 353 (6299), aaf5573

[Non-Patent Document 3] Gootenberg, J S, et al., "Nucleic acid detection with CRISPR-Cas13a/C2c2", Science, 2017 Apr. 28, 356 (6336), p. 438-442

SUMMARY OF THE INVENTION

Technical Problem

However, even if conventional genome editing is applied to phages and used for the treatment of resistant bacteria, CRISPR/Cas9 only cleaves the genomic DNA of the bacteria, so that the bactericidal effect cannot be obtained by the gene repair mechanism of the bacteria themselves. In some cases, it could induce unexpected genetic evolution of the bacteria. Furthermore, the drug resistance gene in the bacteria is often on a plasmid, and in such a case, CRISPR/Cas9 for targeting a genomic DNA does not have any bactericidal effect.

Therefore, more effective phage has been required for the treatment of drug-resistant bacteria, and the like.

The present invention has been made in view of such a situation, and an object of the present invention is to solve the above-mentioned problems.

Solution to Problem

An antibacterial phage according to the present invention includes CRISPR-Cas13a having a target sequence that recognizes a specific gene as a target.

The antibacterial phage according to the present invention is, wherein the target sequence is designed as a spacer sequence for crRNA of 14 to 28 bases.

The antibacterial phage according to the present invention is, wherein the specific gene is an arbitrary gene, and antibacterial target for any bacteria having the specific gene.

The antibacterial phage according to the present invention is, wherein the specific gene is a drug resistance gene or a pathogenic gene having in bacterial genome and/or plasmid for one or any combination of: Methicillin-Resistant *Staphylococcus aureus* (MRSA), Vancomycin-Resistant *Staphylococcus aureus* (VRSA), Vancomycin-Resistant enterococci (VRE), Penicillin-Resistant *Streptococcus Pneumoniae* (PRSP), Multidrug-resistant *Pseudomonas aeruginosa* (MDRP), Multiple Drug-Resistant *Acinetobacter* (MDRA), carbapenem-resistant *Pseudomonas aeruginosa* (CRPA), carbapenem-resistant *Serratia* (CRSA), third-generation cephalosporin-resistant *pneumoniae* (3GCRKP), third-generation cephalosporin-resistant *E. coli* (3GCREC), fluoroquinolone-resistant *E. coli* (FQREC), colistin-resistant *E. coli* (ColR-EC).

The antibacterial phage according to the present invention is, wherein the drug resistance gene or pathogenic gene is one or any combination of: mecA, vanA, vanB, vanC, vanD, vanE, vanG, vanL, vanM, vanN, pbpla, pbp2b, pbp2x, $bla_{IMP}$, $bla_{VIM}$, $bla_{OXA}$, $bla_{SHV}$, $bla_{SME}$, $bla_{NDM}$, $bla_{IMI}$, $bla_{TEM}$, $bla_{CMY}$, $bla_{GES}$, $bla_{CTX\text{-}M}$, $bla_{KPC}$, aac (6'), parC, gyrA, qnrA, mcr, and mutation thereof.

The antibacterial phage according to the present invention is, wherein the specific gene is a toxin gene or a pathogenic gene included in a bacterial genome and/or a plasmid of one or any combination of: *Staphylococcus aureus, Clostridium botulinum, Vibrio cholerae, Escherichia coli, Vibrio parahaemolyticus, Clostridium tetani, Clostridium perfringens,*

*Staphylococcus pyogenes, Clostridium difficile, Bordetella pertussis, Corynebacterium diphtheriae, Shigella dysenteriae, Bacillus anthracis, Pseudomonas aeruginosa, Listeria monocytogenes*, and *Staphylococcus pneumoniae.*

The antibacterial phage according to the present invention is, wherein: the toxin gene includes one or any combination of: enterotoxin, botulinum neurotoxin, cholera toxin, heat-resistant enterotoxin, heat-resistant enterotoxin, heat-labile enterotoxin, Shiga toxin, tetanus toxin, alpha toxin, leucocidin, beta toxin, toxic shock syndrome toxin, streptidine O, erythrogenic toxin, alpha hemolytic toxins, cytotoxic necrotizing factors I, toxin A, toxin B, pertussis toxin, diphtheria toxin, adhesin, secretion (permeation) apparatus, lysates, and gene for producing superantigens.

The antibacterial phage according to the present invention is, wherein the target sequence is a specific 14-28 base sequence of the target gene sequence.

The antibacterial phage according to the present invention is, wherein the target sequence includes: SEQ ID NO: 7, SEQ ID NO: 17, SEQ ID NO: 22, SEQ ID NO: 26, SEQ ID NO: 27, SEQ ID NO: 28, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52.

The antibacterial phage according to the present invention is, wherein the specific gene causes drug resistance by nucleic acid acquisition and/or nucleic acid mutation.

The antibacterial phage according to the present invention is, wherein the target is a plurality of sequences, and each of a plurality of specific genes is recognized as the target.

A therapeutic composition according to the present invention including the antibacterial phage.

A bactericidal agent according to the present invention includes the antibacterial phage.

A food according to the present invention includes the antibacterial phage.

A bacteria identification kit according to the present invention includes the antibacterial phage.

A therapeutic composition manufacturing method according to the present invention including the steps of: transforming and/or infecting a phagemid having CRISPR, Cas13a, and a packaging sequence with a target sequence that recognizes a specific gene as a target, and helper phage with a phage-synthesizing bacteria, and lysing and/or releasing out of the cell; and obtaining constructed antibacterial phage.

A bacteria elimination method according to the present invention including the steps of: applying antibacterial phage including CRISPR-Cas13a having a target sequence that recognizes a specific gene as a target; and eliminating bacteria having the specific gene.

The bacteria elimination method according to the present invention is, wherein the bacteria are present in bacterial flora of humans, animals, and/or an environment.

The bacteria elimination method according to the present invention is, wherein the bacteria are present in food.

A bacteria identification method according to the present invention includes the steps of: infecting bacteria with antibacterial phage including CRISPR-Cas13a having a target sequence that recognizes a specific gene as a target; and determining and/or testing whether the bacteria have the specific gene.

The bacteria identification method according to the present invention is, wherein the antibacterial phage including a sequence of an antibiotic resistance gene.

The bacteria identification method according to the present invention is, wherein the bacteria are bacteria being present in the bacterial flora in humans, animals, foods, or the environment, and/or genetically modified bacteria.

An animal therapeutic method according to the present invention includes: applying antibacterial phage including CRISPR-Cas13a having a target sequence that recognizes a specific gene as a target; treating infectious diseases caused by bacteria having the specific gene in the animal other than a human.

Effect of the Invention

According to the present invention, as configured to include CRISPR-Cas13a having a target sequence that recognizes a specific gene as a target, an antibacterial phage capable of effectively treating drug-resistant bacteria, toxin-producing bacteria, or the like, can be achieved.

BRIEF DESCRIPTION OF THE DRAWINGS

FIG. 2A is a diagram and a photograph showing a bactericidal effect of a bacterium having a specific gene according to Example 1 of the present invention by CRISPR-Cas13a;

FIG. 2B is a diagram and a photograph showing a bactericidal effect of a bacterium having a specific gene according to Example 1 of the present invention by CRISPR-Cas13a;

FIG. 2C is a diagram and a photograph showing a bactericidal effect of a bacterium having a specific gene according to Example 1 of the present invention by CRISPR-Cas13a;

DESCRIPTION OF THE EMBODIMENTS

First Embodiment

Considering the history of antibacterial drug development and the transition of resistant bacteria, the emergence of resistant strains is inevitable, and further, it is feared that there is no evolutionary adaptive drug that can respond to the emergence of new resistant strains. However, CRISPR/Cas9 as described in Patent Document 1 could not be applied to antibacterial treatment.

Therefore, the present inventors sought by using the CRISPR-Cas13a, which is a CRISPR system targeting RNA, described in Non-Patent Document 1. As described in Non-Patent Document 2, Cas13a was discovered in 2015, and its function was elucidated the following year. Although the CRISPR-Cas13a targets the RNA, Cas13a enzyme recognizes once a target RNA in a sequence-specific manner, and it rapidly changes the enzyme to degrade the various RNA sequence-nonspecifically. Therefore, Non-Patent Document 3 shows a method for detecting RNA degraded by Cas13a in order to detect DNA of an infectious pathogen. This method is just a detection method that is performed after extracting nucleic acid from bacteria, and it is completely unrelated to antibacterial treatment.

Actually, Cas13a of Non-Patent Document 2 uses a method of transforming a plasmid into bacteria, and therefore it cannot be applied to antibacterial treatment.

On the other hand, the present inventors considered the possibility of introducing the CRISPR-Cas13a into bacterial cells and using it as a bactericidal agent. Specifically, the present inventor has a conception of producing antibacterial phage, which is an artificially designed and manufactured synthetic phage, by designing CRISPR-Cas13a having a target sequence (target gene recognition sequence) that recognizes a resistance gene sequence, or the like, and by including (loading) the DNA encoding this in the phage, and the present invention is completed by repeating diligent experiments.

Figure 1:
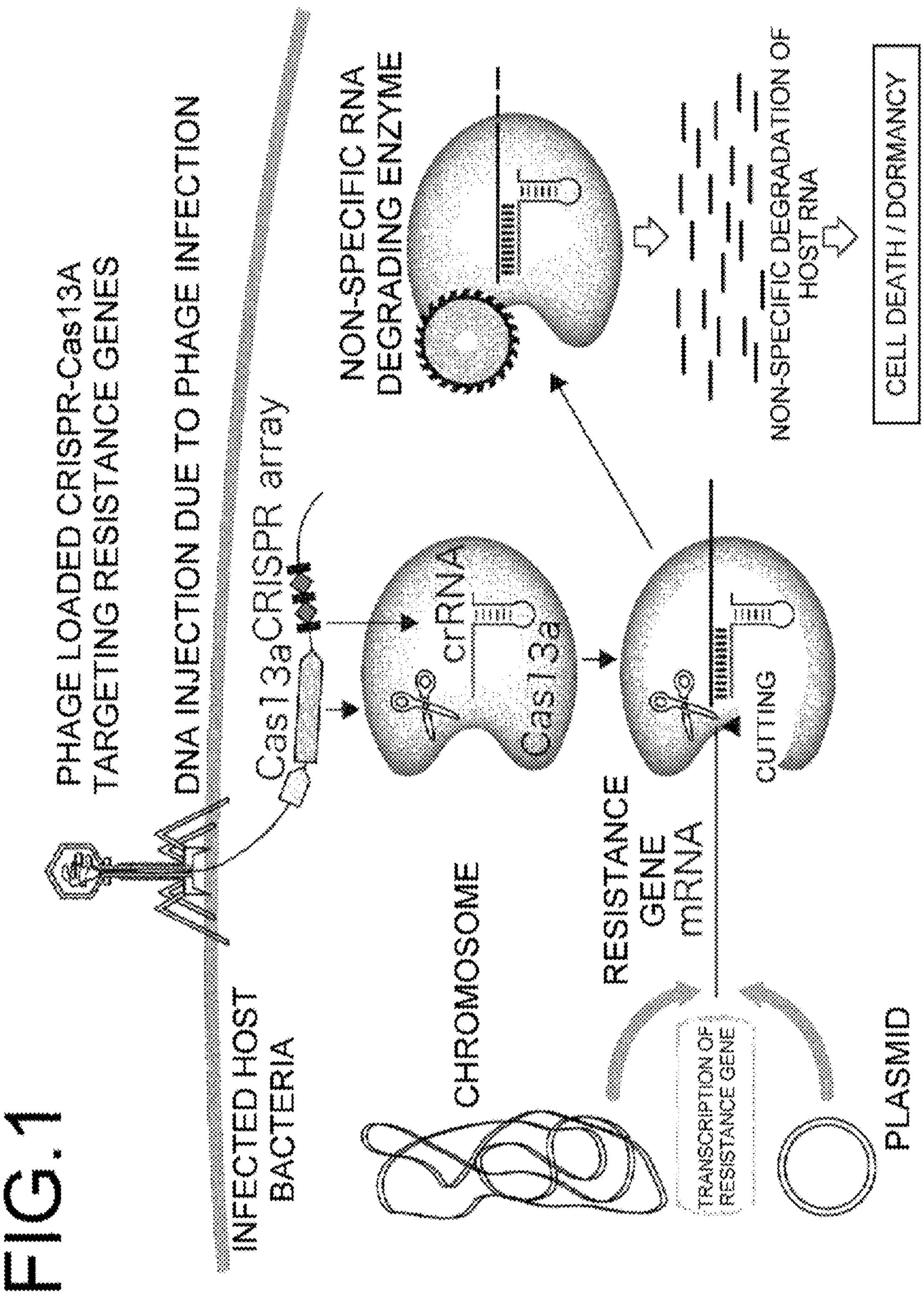
FIG. 1 is a conceptual diagram of an antibacterial treatment method by using antibacterial phage according to the first embodiment of the present invention.

FIG. 1 shows the concept of an antibacterial treatment method by using antibacterial phage containing CRISPR-Cas13a of the present embodiment.

The antibacterial phage of the present embodiment utilizes the specific nucleotide sequence recognition of CRISPR and the non-specific nucleotide sequence RNA degradation activity of Cas13a. When the antibacterial phage of the present embodiment is infected with a target bacterium, Cas13a synthesized in the bacterium recognizes and cleaves the resistance gene mRNA derived from a chromosome or a plasmid. Cas13a incorporating the target sequence is transformed into a non-specific RNA-degrading enzyme, which induces cell death or dormancy associated with degradation of the host bacterial RNA. That is, by loading CRISPR-Cas13a DNA having a DNA sequence of a target sequence of about 20 bases on an antibacterial phage, antibacterial treatment that selectively kills only a specific bacterium having a specific gene becomes possible.

Hereinafter, an antibacterial phage, a therapeutic composition, a bactericidal agent, a food, a bacterial identification kit, a therapeutic composition manufacturing method, a bacteria elimination method, a bacteria identification method, and an animal therapeutic method according to the present embodiment is specifically described in detail.

The antibacterial phage according to the first embodiment of the present invention is characterized in that including CRISPR-Cas13a having a target sequence that recognizes a specific gene as a target.

Here, the specific gene of the present embodiment is an arbitrary gene that makes the bacterium distinguishable into a specific genotype. The specific genotype may be, for example, even in the same type of bacterium, sufficient to be capable for identifying by the gene sequence of genomic DNA, plasmid in the bacterium, other gene not in the genome, or the like, and the phenotype does not necessarily have to be different. Further, the specific gene of the present embodiment may be a bacterium gene itself, a recombinant gene, a gene introduced into a genome, a plasmid, or the like. Furthermore, the specific gene does not necessarily have to be translated into a protein.

More specifically, the specific gene of the present embodiment may be, for example, a drug resistance gene of a drug-resistant bacterium, a various toxin gene, a gene encoding proteins associated with being weak virulent or strong virulent, an enzyme gene for producing a specific metabolite, a gene for identifying the bacterium, a reporter gene used for transformation, a sequences having restriction enzymes and sticky ends used for genetic modification, a repeat sequence, a "gene" indicating another genotype in a broad sense.

That is, the antibacterial phage of the present embodiment can target a bacterium having any specific gene, such as a bacterium having a specific virulence factor, or the like, by changing the design target sequence.

As a specific example, when this specific gene is a drug resistance gene, it may be included in the genome and/or a plasmid of a bacterium having one or any combination of the group including: a various pathogenic *E. coli* strain (*Escherichia coli*), methicillin-resistant *Staphylococcus aureus* (MRSA), vancomycin-resistant *Staphylococcus aureus* (VRSA), vancomycin-resistant enterococci (VRE), penicillin-resistant *Streptococcus pneumoniae* (PRSP), multidrug-resistant *Pseudomonas aeruginosa* (MDRP), multidrug-resistant *Acinetobacter* (MDRA), multidrug-Resistant *Acinetobacter*, carbapenem-resistant *Pseudomonas aeruginosa* (CRPA), carbapenem-resistant *Serratia* (CRSA), third generation cephalosporin-resistant *Klebsiella pneumoniae*

(3GCRKP), 3rd generation cephalosporin-resistant *E. coli* (3GCREC), fluoroquinolone-resistant *E. coli* (FQREC), colistin resistant *E. coli* (ColR-EC).

target RNA), and phages for antibacterial phage used in this embodiment (bacteriophage) are summarized and shown in Table 1 below:

TABLE 1

| TARGET RNA | | | |
|---|---|---|---|
| No. | TYPES OF RESISTANT BACTERIA | GENE NAME ENCODING TARGET RNA | TYPES OF BACTERIOPHAGE (ABOUT 2-3 TYPES) |
| 1 | METHICILLIN-RESISTANT *STAPHYLOCOCCUS AUREUS* (MRSA) | mecA | NM1, SaPIbov1, SaPIbov2, SaPI1, K, S25-1, S24-3, 80α, OTHER LYSOGENIZED PHAGE |
| 2 | VANCOMYCIN-RESISTANT *STAPHYLOCOCCUS AUREUS* (VRSA) | vanA, vanB | NM1, SaPIbov1, SaPIbov2, SaPI1, K, S25-1, S24-3, 80α, OTHER LYSOGENIZED PHAGE |
| 3 | VANCOMYCIN-RESISTANT ENTEROCOCCI (VRE) | vanA, vanB, vanC, vanD, vanE, vanG, vanL, vanM, vanN | φEf11, V583, OTHER LYSOGENIZED PHAGE |
| 4 | PENICILLIN-RESISTANT *STREPTOCOCCUS PNEUMONIAE* (PRSP) | pbp1a, pbp2b pbp2x | Dp-1, HB-1, EJ-1, OTHER LYSOGENIZED PHAGE |
| 5 | MULTIDRUG-RESISTANT *PSEUDOMONAS AERUGINOSA* (MDRP) | bla$_{IMP[NOTE1]}$ bla$_{VIM[NOTE2]}$, bla$_{OXA[NOTE6]}$, aac(6'), parC, gyrA | gh-1, philBB-PF7A, phil5, KPP12, OTHER LYSOGENIZED PHAGE |
| 6 | MULTIPLE DRUG-RESISTANT ACINETOBACTER (MDRA) | bla$_{IMP[NOTE1]}$ bla$_{SHV[NOTE8]}$, bla$_{SME[NOTE10]}$, aac(6'), gyrA, parC | IsxxfAB78, F1245/05, OTHER LYSOGENIZED PHAGE |
| 7 | CARBAPENEM-RESISTANT *PSEUDOMONAS AERUGINOSA* (CRPA) | bla$_{IMP[NOTE1]}$, bla$_{VIM[NOTE2]}$, bla$_{NDM[NOTE3]}$, bla$_{IMI[NOTE7]}$, | gh-1, philBB-PF7A, phi15, OTHER LYSOGENIZED PHAGE |
| 8 | CARBAPENEM-RESISTANT *SERRATIA* (CRSA) | bla$_{TEM[NOTE9]}$, bla$_{CMY[NOTE12]}$, bla$_{GES[NOTE5]}$ | phiMAM1, CBH8, OTHER LYSOGENIZED PHAGE |
| 9 | THIRD-GENERATION CEPHALOSPORIN-RESISTANT *PNEUMONIAE* (3GCRKP) | bla$_{CTX\text{-}M[NOTE11]}$, bla$_{TEM[NOTE9]}$, bla$_{KPC[NOTE4]}$, bla$_{SHV[NOTE8]}$ | K11, KP32, vB_Klox-2, OTHER LYSOGENIZED PHAGE |
| 10 | THIRD-GENERATION CEPHALOSPORIN-RESISTANT *E. COLI* (3GCREC) | bla$_{IMP[NOTE1]}$ | M13, T6, 80, λ, OTHER LYSOGENIZED PHAGE |
| 11 | FLUOROQUINOLONE-RESISTANT *E. COLI* (FQREC) | gyrA, parC, qnrA | M13, T6, 80, λ, OTHER LYSOGENIZED PHAGE |
| 12 | COLISTIN-RESISTANT *E. COLI* (COLR-EC) | mcr$_{[NOTE13]}$ | M13, T6, 80, λ, OTHER LYSOGENIZED PHAGE |

NOTE 1.
bla$_{IMP}$: bla$_{IMP\text{-}1}$, bla$_{IMP\text{-}6}$, bla$_{IMP\text{-}7}$, bla$_{IMP\text{-}10}$, bla$_{IMP\text{-}11}$, bla$_{IMP\text{-}15}$, bla$_{IMP\text{-}19}$, bla$_{IMP\text{-}31}$, bla$_{IMP\text{-}35}$, bla$_{IMP\text{-}37}$.
NOTE 2.
bla$_{VIM}$: bla$_{VIM\text{-}1}$, bla$_{VIM\text{-}2}$, bla$_{VIM\text{-}4}$, bla$_{VIM\text{-}5}$, bla$_{VIM\text{-}7}$, bla$_{VIM\text{-}10}$, bla$_{VIM\text{-}18}$, bla$_{VIM\text{-}19}$, bla$_{VIM\text{-}25}$.
NOTE 3.
bla$_{NDM}$: bla$_{NDM\text{-}1}$, bla$_{NDM\text{-}2}$, bla$_{NDM\text{-}3}$, bla$_{NDM\text{-}4}$, bla$_{NDM\text{-}5}$, bla$_{NDM\text{-}6}$, bla$_{NDM\text{-}7}$, bla$_{NDM\text{-}8}$, bla$_{NDM\text{-}9}$, bla$_{NDM\text{-}10}$.
NOTE 4.
bla$_{KPC}$: bla$_{KPC\text{-}1}$, bla$_{KPC\text{-}2}$, bla$_{KPC\text{-}3}$, bla$_{KPC\text{-}5}$, bla$_{KPC\text{-}7}$, bla$_{KPC\text{-}10}$, bla$_{KPC\text{-}11}$, bla$_{KPC\text{-}14}$, bla$_{KPC\text{-}15}$.
NOTE 5.
bla$_{GES}$: bla$_{GES\text{-}2}$, bla$_{GES\text{-}4}$, bla$_{GES\text{-}5}$, bla$_{GES\text{-}18}$.
NOTE 6.
bla$_{OXA}$: bla$_{OXA\text{-}11}$, bla$_{OXA\text{-}15}$, bla$_{OXA\text{-}23}$, bla$_{OXA\text{-}24}$, bla$_{OXA\text{-}48}$, bla$_{OXA\text{-}58}$, bla$_{OXA\text{-}146}$, bla$_{OXA\text{-}162}$, bla$_{OXA\text{-}181}$.
NOTE 7.
bla$_{IMI}$: bla$_{IMI\text{-}1}$, bla$_{IMI\text{-}2}$, bla$_{IMI\text{-}3}$.
NOTE 8.
bla$_{SHV}$: bla$_{SHV\text{-}1}$, bla$_{SHV\text{-}10}$.
NOTE 9.
bla$_{TEM}$: bla$_{TEM\text{-}1}$, bla$_{TEM\text{-}10}$, bla$_{TEM\text{-}30}$.
NOTE 10.
bla$_{SME}$: bla$_{SME\text{-}1}$, bla$_{SME\text{-}2}$, bla$_{SME\text{-}3}$.
NOTE 11.
bla$_{CTX\text{-}M}$: bla$_{CTX\text{-}M\text{-}1}$, bla$_{CTX\text{-}M\text{-}2}$, bla$_{CTX\text{-}M\text{-}9}$, bla$_{CTX\text{-}M\text{-}19}$.
NOTE 12.
bla$_{CMY}$: bla$_{CMY\text{-}1}$, bla$_{CMY\text{-}2}$.
NOTE 13.
mcr: mcr$_{-1}$, mcr$_{-2}$., mcr$_{-3}$.

In this case, these drug resistance genes includes any one or any combination of the group: mecA, vanA, vanB, vanC, vanD, vanE, vanG, vanL, vanM, vanN, pbpla, pbp2b, pbp2x, bla$_{IMP}$, bla$_{VIM}$, bla$_{OXA}$, bla$_{SHV}$, bla$_{SME}$, bla$_{NDM}$, bla$_{IMI}$, bla$_{TEM}$, bla$_{CMY}$, bla$_{GES}$, bla$_{CTX\text{-}M}$, bla$_{KPC}$, aac (6'), parC, gyrA, qnrA, mcr, and a type of mutation thereof.

Examples of these drug-resistant bacteria (types of resistant bacteria), drug-resistant genes (gene names encoding As shown in this table, drug resistance genes include their respective mutants (variations).

In addition, these drug resistance genes may be horizontally transmitted to other kind of bacteria, which the classification as bacteria may be different.

In addition, the specific gene may be one that causes drug resistance by nucleic acid acquisition and/or nucleic acid mutation.

Specifically, since resistant bacteria may be originated by acquisition of foreign DNA or RNA (nucleic acid) and/or nucleic acid mutation, the nucleic acid mutation may be a specific gene targeted by the antibacterial phage according the present embodiment. In this case, the antibacterial phage of the present embodiment can counter the bacteria having the nucleic acid mutation that has caused drug resistance as the "specific gene" by modifying the target sequence in response to this mutation.

Further, the target sequence of the antibacterial phage according to the first embodiment of the present invention is characterized by being a base sequence designed to recognize the specific gene as a target. On this basis, when the target sequence of the present embodiment is designed as a spacer sequence of crRNA of 14 to 28 bases, it is preferable that the target at the 10th base in the DNA base sequence when packaged in the antibacterial phage is T. Specifically, the target sequence may be, for example, SEQ ID NO: 7, SEQ ID NO: 17, SEQ ID NO: 22, SEQ ID NO: 26, SEQ ID NO: 27, SEQ ID NO: 28, and SEQ ID NO: 36.

Here, as shown in the following example, in the antibacterial phage having CRISPR-Cas13a of the present embodiment, even if a location at a random position within the specific gene is simply selected as the crRNA sequence, there is a difference in the bactericidal effect. For this reason, as a result of diligent experiments conducted by the present inventors, we have found that it is possible to optimize the efficiency of non-specifically degrading the RNA of Cas13a to cause the bacterium to be cell-death by using a sequence in which the 10th base is T (thymine) on the 5 ' to 3' side as a crRNA spacer sequence of 14 to 28 bases in the DNA base sequences in the specific gene. As an example of such a sequence, each nucleic acid sequence of SEQ ID NO: 7, SEQ ID NO: 17, SEQ ID NO: 22, SEQ ID NO: 26, SEQ ID NO: 27, SEQ ID NO: 28, and SEQ ID NO: 36 in the following sequence listing is shown. Furthermore, as a specific example, the base sequence of crDNA loaded in the antibacterial phage may be designed as a complementary sequence as shown in the following examples. In addition, when crDNA targets a transcribed RNA, the target in the RNA is U (Uracil).

Furthermore, as shown in the second embodiment as described later, sequences other than these may be accepted as target sequences of antibacterial phage.

In addition, there are a plurality of target sequences, and a plurality of specific genes may be configured to be recognized as targets. That is, the antibacterial phage of the present embodiment can have a plurality of target sequences in one phage. At this time, since it is possible to include about 1 to a dozen spacer sequences of CRISPR, a plurality of target sequences may be included within the range that can be included in the capsid of the phage. The plurality of target sequences may be arranged consecutively or as a plurality of sites in the sequence of crRNA, or it may be configured to have a plurality of crRNAs having different target sequences in the phage. This makes it possible to apply one antibacterial phage to a plurality of resistant bacteria. Furthermore, in the case of multidrug-resistant bacteria having a plurality of resistance genes, it is possible to improve the antibacterial efficiency by CRISPR-cas13a.

Further, the antibacterial phage according to the first embodiment of the present invention can also be used for the use of a therapeutic composition including the antibacterial phage. That is, by administering the antibacterial phage of the present embodiment for treatment, it can be used in an antibacterial treatment method for selectively killing a specific genotype bacterium. Specifically, CRISPR-Cas13a DNA that specifically recognizes the target RNA is synthesized and packaged in antibacterial phage (included in the capsid) to selectively kill the target (having a specific gene) bacterium, and an antibacterial treatment method can be realized. This makes it possible to enable antibacterial treatment of infectious diseases that are difficult to treat with antibacterial agents, including infectious diseases of drug-resistant bacteria.

In this therapeutic composition manufacturing method, the steps of: transforming and/or infecting a phagemid having CRISPR, Cas13a, and a packaging sequence with the target sequence that recognizes a specific gene as a target, and helper phage with a phage-synthesizing bacteria, and lysing and/or releasing out of the cell, and obtaining constructed antibacterial phage are included.

Specifically, in the therapeutic composition of the present embodiment, it is possible to use synthesized CRISPR-Cas13a DNA that specifically recognizes the target RNA, which is loaded into antibacterial phage (packaging, included in capsid), and various formulations similar to the conventional antibacterial treatment method by using antibacterial phage (antibacterial phage therapy). As the phage synthesizing bacterium, for example, a general bacterium such as *E. coli*, or the like, can be used.

In addition, the therapeutic composition according to the first embodiment of the present invention can be administered together with any pharmaceutically acceptable carrier composition. Examples of the carrier composition include isotonic solutions containing physiological saline, glucose and other adjuvants, such as D-sorbitol, D-mannose, D-mannitol, sodium chloride and the like, suitable solubilizers such as alcohols, specifically ethanol, poly-alcohols such as propylene glycol, polyethylene glycol, nonionic surfactants such as polysorbate 80 (TM), HCO-50, and the like, can be mentioned, and, however, it is not limited to them. In addition, suitable excipients, and the like, may be further included.

Also, the therapeutic compositions of this embodiment may include suitable pharmaceutically acceptable carriers for preparing a pharmaceutically acceptable carrier composition. The carrier may include biocompatible materials such as silicone, collagen, gelatin, or the like. Alternatively, it may be various emulsion liquid. Further, for example, one or more pharmaceutical additives selected from diluents, fragrances, preservatives, excipients, disintegrants, lubricants, binders, emulsifiers, plasticizers, and the like may suitably be included.

The therapeutic composition according to the first embodiment of the present invention may be formulated in a dosage form suitable for administration for oral administration, by using a pharmaceutically acceptable carrier well known in the art.

The way of administration of the pharmaceutical composition according to the present invention is not particularly limited, and oral administration or non-oral administration is possible. The non-oral administration can be, for example, intravenous, intraarterial, subcutaneous, intradermal, intramuscular, intraperitoneal administration, or direct administration to the bacterial flora or infected site. The administration method may be carried out in the same manner as typical phage therapy.

Further, in order to use the therapeutic composition according to the first embodiment of the present invention for the above-mentioned treatment, the administration interval and the dose can appropriately be selected and changed according to various conditions such as the condition of the disease and the condition of the subject.

The single dose and the number of administrations of the therapeutic composition according to the first embodiment of the present invention can be selected and changed as appropriate depend on the purpose of administration and further depending on various conditions such as the age and weight of the patient, symptoms and severity of disease.

The number and duration of administration may be only once, or may be administered once to several times a day for several weeks, the state of the disease may be monitored, and the administration may be performed again or performed repeatedly depending on the state.

The composition of the present invention can also be used in combination with other compositions, and the like. Further, the composition of the present invention may be administered at the same time as other compositions, or may be administered at intervals, but the order of administration is not particularly limited. Further, in the first embodiment of the present invention, the period during that the disease is improved or alleviated is not particularly limited, but may be temporary improvement or alleviation, or may be improvement or alleviation for a certain period.

In addition, the therapeutic composition of the first embodiment of the present invention can be the subject of treatment for an organism, a part of the body of the organism, or a part thereof extracted or excreted from the organism. This organism is not particularly limited and may be, for example, animals, plants, fungi, or the like. These animals include, for example, humans, livestock animal species, wild animals, or the like. Therefore, the therapeutic composition according to the first embodiment of the present invention can also be used for animal treatment for treating animals. That is, the antibacterial phage of the present embodiment can also be used in an animal treatment method for various animals other than humans.

Specifically, in the animal therapeutic method of the present embodiment, it is possible to treat infectious diseases caused by bacteria having the specific gene in animals other than by humans using antibacterial phage including CRISPR-Cas13a having a target sequence that recognizes the specific gene as the target.

The animal is also not particularly limited, and it includes a wide range of vertebrates and invertebrates. The vertebrates include fish, amphibians, reptiles, birds, and mammals. Specifically, for example, the mammals may include rodents, such as mice, rats, hamsters, guinea pigs, or rabbits, ferrets, dogs, cats, sheep, pigs, cows, horses, or non-human transgenic primates. In addition to the mammals, wild animals include fish, birds including poultry, reptiles, or the like. They also include a wide range of crustaceans including shrimp and insects, and other invertebrates such as squid. That is, the therapeutic composition according to the first embodiment of the present invention can be used not only for human treatment but also for animal treatment, livestock growth promotion, and the like.

Further, the bacteria elimination method according to the first embodiment of the present invention is characterized in that includes the steps of: applying antibacterial phage including CRISPR-Cas13a having a target sequence that recognizes a specific gene as a target; and eliminating bacteria having the specific gene. Therefore, the composition including the antibacterial phage of the present embodiment can be used as the bactericidal agent (growth inhibitor). The bactericidal agent can also be included in an appropriate carrier, solution, or the like, as described above. It is also possible to add an auxiliary agent that eliminates bacterial peptidoglycan, biofilm, or the like. The bactericidal agent may be provided by being included in various antibacterial products such as hand wash solutions, mouthwashes, masks and napkins, air purifier filters, and the like.

By applying, spraying, or the like, the bactericidal agent according to the present embodiment, it is possible to eliminate specific genotype bacteria and suppress their growth from the focus of infection, bacterial flora, and environment. That is, it is possible to reduce bacteria having a specific gene present in the bacterial flora in humans, animals, and/or the environment.

In addition, in the bacteria elimination method according to the first embodiment of the present invention, it is also possible to eliminate bacteria existing in food. This is because the antibacterial phage of the present embodiment does not infect humans. That is, the antibacterial phage of the present embodiment can selectively eliminate a specific genotype bacterium having a specific gene in food. Further, it is also possible to provide foods from which specific genotype bacteria have been eliminated in this way. This makes it possible to provide, for example, a safe food from which food poisoning bacteria that produce toxins have been reliably eliminated. Here, the antibacterial phage of the present embodiment can be used by being included in any of food cultivation, culture fishery, harvesting, or the like, including various vegetables, meat, seafood, processed foods, dairy products, and the like.

In addition, the bacteria identification method including the steps of: infecting bacteria with antibacterial phage including CRISPR-Cas13a having a target sequence that recognizes a specific gene as a target; and determining and/or testing whether the bacteria have the specific gene. Specifically, by designing CRISPR-Cas13a targeting the specific gene, loading it on the antibacterial phage of the present embodiment, and selectively killing the bacteria having the specific gene, the bacteria that has the specific gene and is the specific genotype can be easily detected. That is, the antibacterial phage of the present embodiment can also be used for identification and inspection.

Specifically, for example, by being the increase (growth) in the number of bacteria suppressed after simultaneously adding the target bacterium and the antibacterial phage of the present embodiment, or, by culturing on a plate, applying the antibacterial phage of the present embodiment, and confirming lysis, it is possible to easily determine (test) whether or not the specific gene is present in the bacterium. The specific gene that can be identified by this bacterial identification method may be the specific gene targeted by the above-mentioned bacterial elimination method.

As described above, the bacterium to be identified and/or tested by this bacteria identification method may be a bacteria present in the bacterial flora in humans, animals, foods, or the environment, and/or a genetically modified bacterium. It is also possible to provide a bacterial identification kit including the antibacterial phage according to the present embodiment.

As configured in this way, the following effects can be obtained.

Traditionally, antibacterial agents have played the most important role in the treatment of bacterial infections. However, due to the emergence of drug-resistant bacteria for which antibacterial drugs do not work and their rapid spread, existing antibacterial agents are being neutralized. For this reason, bacterial infections have become a global problem that threatens human health again. Specifically, the problem of resistant bacteria has become unsolvable due to the emergence of resistant bacteria at a speed far faster than the development of antibacterial drugs and the stalemate in the development of new antibacterial drugs.

On the other hand, the antibacterial phage according to the first embodiment of the present invention, by loading CRISPR-Cas13a on the antibacterial phage, it is possible to deal with resistant bacteria without using antibacterial agents. That is, since the specific gene targeted by CRISPR-Cas13a can be arbitrarily determined, bacteria of any specific genotype can be a sterilized target.

Further, since the antibacterial phage of the present embodiment targets the RNA transcribed by CRISPR-Cas13a, it is possible to effectively sterilize the target specific gene regardless of whether it is in a chromosome or a plasmid.

Further, since the antibacterial phage of the present embodiment targets RNA, evolutionary selective pressure is hard to apply, and resistant bacteria are less likely to be generated in principle. Furthermore, even for bacteria that are not sterilized due to different specific genotypes, antibacterial phage corresponding to the specific gene of such specific genotype may be designed and applied. Therefore, by appropriately selecting a specific gene to produce an antibacterial phage, it is possible to surely kill the specific genotype bacterium. That is, the antibacterial phage according to the first embodiment of the present invention can be an evolutionary adaptive drug that can respond by redesigning only the sequence recognition portion of CRISPR-Cas13a when a new resistant bacterium is generated. Also, it is also possible to modify the loaded antibacterial phage itself by using genetic engineering technology.

Further, in the antibacterial treatment method by using an antibacterial agent, there is a problem that the antibacterial range of the antibacterial agent, that is, the range of target bacteria exerting a bactericidal effect is wide, and the selectivity is low. For this reason, bacteria other than the target bacteria also have an antibacterial effect, and bacteria resistant to antibacterial agents have been selected, leading to induction of drug resistance, and the like. In addition, this also affected the balance of the host's normal flora by killing a wide range of bacteria.

On the other hand, in the antibacterial phage according to the first embodiment of the present invention, CRISPR-Cas13a can recognize a target sequence of about 20 bases, and this recognition requires almost 100% sequence homology. This selectivity enables highly selective antibacterial treatment that kills only the target bacteria. As a result, useful indigenous bacteria, and the like, are not sterilized, and the balance of the normal bacterial flora of the host can be maintained. In addition, by introducing CRISPR-Cas13a into infected bacterial cells via antibacterial phage limited by the bacterial species to be infected, the selectivity of the target bacterium can be further enhanced. That is, CRISPR-Cas13a recognizes and activates the target RNA sequence, enabling "tracking missile-type" antibacterial therapy that can selectively eliminate only specific genotype bacteria from the bacterial flora. Furthermore, it is possible to establish an antibacterial treatment method that can be applied to all bacterial species in humans, animals, and the environment.

Further, in the present embodiment, since the antibacterial phage, which is a synthetic phage that does not self-proliferate, is used, side effects due to mutation of the antibacterial phage itself can be suppressed. In addition, since the antibacterial phage does not self-proliferate, the possibility that the prophage is retained by the administered organism or bacteria in the environment is extremely low. Furthermore, in principle, resistant bacteria are less likely to occur. This enhances safety. Furthermore, even if the target gene is mutated, it can be dealt with by changing the probe (crRNA sequence) that recognizes the target RNA each time. In addition, since it is an antibacterial phage that does not self-proliferate, it is possible to accurately estimate the administration dose.

In addition, the antibacterial phage according to the first embodiment of the present invention can control gene expression in specific cells in a living body, and thus not only does it help clarify the physiological functions of cells, but it may also lead to the control of pathological conditions. This may lead to the development of new treatments.

Further, the antibacterial phage according to the first embodiment of the present invention only kills bacteria having a specific gene, and in addition, since it is derived from a natural substance, it is safe and has a low environmental load. Therefore, it is possible to provide safe and environmentally friendly bactericide and food.

In addition to treatment, the antibacterial phage according to the first embodiment of the present invention can also be applied to a bacterial identification method for detecting (identifying) a specific gene with high sensitivity. This makes it possible to reliably determine whether or not a specific resistance gene is present in, for example, a clinically isolated bacterium such as *Escherichia coli*, or the like. In such a case, it does not take time and effort because it is only visually observed that the bacteria do not grow or lyse, and since the amplification of nucleic acid is not required, it is not necessary to use a device such as PCR, so that it can become identified at low cost.

Second Embodiment

Next, as a second embodiment of the present invention, an example of producing an antibacterial phage, which is an artificially designed and manufactured synthetic phage, is described. In the example, a CRISPR-Cas13a having a target sequence (target gene recognition sequence) that recognizes a toxin gene as a specific gene is designed, and a DNA encoding this is included (loaded) in the phage.

As a specific example, when this specific gene is a toxin gene, it may be included in a bacterial genome and/or plasmid having one or any combination of groups including: *Staphylococcus aureus, Clostridium botulinum, Vibrio cholerae, Escherichia coli, Vibrio parahaemolyticus, Clostridium tetani, Clostridium perfringens*, Group A *streptococcus* (*Streptococcus pyogenes*), *Clostridium difficile, Bordetella pertussis*, Diphtheria (*Corynebacterium diphtheriae*), *Shigella dysenteriae, Bacillus anthracis, Pseudomonas aeruginosa, Listeria monocytogenes, Streptococcus pneumoniae* (*Staphylococcus pneumoniae*).

In this case, the toxin gene includes one kind or any combination of the group including: enterotoxin, botulinum neurotoxin, cholera toxin, heat-resistant enterotoxin, heat-labile enterotoxin, thermostable direct hemolysin, Shiga toxin, tetanus toxin, alpha toxin, leucocidin, beta toxin, toxic shock syndrome toxin, streptidine O, erythrogenic toxin, alpha hemolytic toxins, cytotoxic necrotizing factors I, toxin A, toxin B, pertussis toxin, diphtheria toxin, adhesin, secretion (permeation) apparatus, lysates, and gene for producing superantigens.

The types of these toxin-producing bacteria (types of bacteria), toxin genes (gene names encoding target RNA), and phages for antibacterial phage (bacteriophage) used in this embodiment are summarized in Table 2 below.

TABLE 2

| No. | BACTERIAL SPECIES | TOXIN |
|---|---|---|
| 1 | *Staphylococcus aureus* | enterotoxins, Toxic shock syndrome toxin (TSST-1), Exfoliatin toxin, alpha toxin, beta toxin, leukocidin |
| 2 | *Clostridium botulinum* | Botulinum toxin |
| 3 | *Vibrio cholerae* | Cholera enterotoxin (ctx) |
| 4 | *Escherichia coli* | *E. coli* LT toxin, *E. coli* ST toxin, hemolysin, Shiga toxin |
| 5 | *Vibrio parahaemolyticus* | thermostable direct hemolysin (TDH), TDH-related hemolysin (TRH) |
| 6 | *Clostridium tetani* | Tetanus toxin |
| 7 | *Clostridium perfringens* | Perfringens enterotoxin, perfingiolysin O |
| 8 | *Staphylococcus pyogenes* | Erythrogenic toxin (streptococcal pyrogenic exotoxin SPE), streptolysin O |
| 9 | *Clostridium difficile* | toxin A, toxin B |
| 10 | *Bordetella pertussis* | Pertussis toxin (ptx), Adenylate cyclase toxin |
| 11 | *Corynebacterium diphtheriae* | Diphtheria toxin (dtx) |
| 12 | *Shigella dysenteriae* | Shiga toxin |
| 13 | *Bacillus anthracis* | Anthrax toxin (LF), Anthrax toxin (EF) |
| 14 | *Pseudomonas aeruginosa* | Exotoxin A |
| 15 | *Listeria monocytogenes* | listeriolysin |
| 16 | *Staphylococcus pneumoniae* | pneumolysin |

As shown in this table, each of these toxin genes may have a genetic mutation (variation).

In addition, these toxin genes may be horizontally transmitted to other types of bacteria and may be classified differently as bacteria.

Further, the specific gene of the present embodiment may be a gene that causes a toxin by acquisition of nucleic acid.

Specifically, since the toxin-producing bacterium may be generated by the acquisition of foreign DNA or RNA (nucleic acid), this mutation by nucleic acid may be targeted to be the specific gene for the antibacterial phage of the present embodiment. In this case, the antibacterial phage of the present embodiment can counteract the bacterium having the nucleic acid mutation that is produced the toxin as the "specific gene" by modifying the target sequence in response to this mutation.

The therapeutic composition, the treatment composition, the bactericide, the food, the bacterial identification kit, the therapeutic composition manufacturing method, the bacterial elimination methods, the bacterial identification method, and the animal therapeutic methods by using the antibacterial phage utilizing the toxin gene as the specific gene can be realized in the similar manner as in the first embodiment described above, and the similar effect can be obtained.

For example, in the animal therapeutic method of the present embodiment, it is possible to treat infectious diseases caused by bacteria carrying a specific gene in an animal other than a human by using antibacterial phage having CRISPR-Cas13a with the target sequence that recognizes the toxin gene as the target of the specific gene.

In addition, the antibacterial phage of the present embodiment may have a sequence of an antibiotic resistance gene. On this basis, it is also possible to determine and/or test whether or not the bacterium has the specific gene by using a medium including the antibiotic resistance gene.

Specifically, as shown in Example 2 described later, the antibacterial phage having the antibiotic resistance gene and is cultured on a plate containing and/or not containing this antibiotic, and this makes possible to determine and/or test whether the bacteria have the specific gene.

By incorporating an antibiotic resistance gene into an antibacterial phage, when cultured on a plate containing an antibiotic, the antibacterial phage is infected and only bacteria not having the specific gene grow. On the other hand, bacteria that have not been infected with the antibacterial phage cannot grow because of the antibiotics, and even if infected with antibacterial phage, bacteria having the specific gene is lysed. Here, the drug resistance gene, the toxin gene, or the pathogenic gene, which is detected as a specific gene, targets a gene other than the antibiotic resistance gene having in the antibacterial phage.

As configured in this way, it is possible to increase the detection sensitivity of a specific gene by antibacterial phage by about 100 times or more as compared with culturing in a medium containing no antibiotic.

In addition, in the above-mentioned first embodiment and the second embodiment, an example in which a drug resistance gene or a toxin gene is targeted as a specific gene has been described. Also, as for bacteria, an example of application to bacteria having such drug resistance gene is described.

However, the specific gene is an arbitrary gene, and any bacterium having the specific gene can be an antibacterial target.

That is, any gene that can be distinguished as the above-mentioned specific genotype can be targeted as the specific gene of the present embodiment. In addition, any bacterium having the specific gene can be targeted without specifying the bacterium. Specifically, as an example, any of *Shigella* (*Shigella* dysenteria) and enterohemorrhagic *Escherichia coli* (*E. coli*, EHEC) having the same specific gene of verotoxin can be targeted for antibacterial activity. In such a case, all the bacteria having a specific genotype can be made antibacterial by making the phage so that a plurality of bacteria are targeted at the same time.

Furthermore, the specific gene may include a gene that is expressed, regulated expression, or associated with a drug resistance gene or a toxin gene. In addition, the particular gene may have a pathogenic gene associated with the other pathogenicity.

In addition, the probe (crRNA sequence) that recognizes the target RNA of CRISPR-Cas13a according to the first embodiment and the second embodiment of the present invention can identify even a single base difference in the base sequence. Therefore, it can be applied to treatment of a cancer or a hereditary disease. In this case, it is possible to use not necessarily Cas13a for bacteria, but a similar enzyme that induces apoptosis, or the like, by non-specific RNA degradation action in cells other than eubacteria and leads to cell death.

Furthermore, the specific gene of the present embodiment may be a "gene" in a broad sense such as a sequence of a gene mutation targeted for cancer treatment or a hereditary disease, a single nucleotide substitution (SNP), or a repeat sequence. In this case, the bacterium itself can be administered therapeutically as a carrier of the drug. That is, it can also be applied to an application that a drug corresponding to the cell of the specific gene is contained in the cytoplasm of the target bacterium, or the like, and is dispersed around a tissue and target cells by lysis. In such case, it is also possible to provide the bacterium itself including the prophage. Further, it may also include prophage that is activated by a particular immune response.

Further, in the above-mentioned first embodiment and the second embodiment, an example in which a general bacteriophage is used as an antibacterial phage has been described. However, as the "antibacterial phage", it is also possible to use a virus, RNA virus, phagemid, or the like, which infects bacteria and is different from a general bacteriophage. In addition, the antibacterial phage may be provided in the state of prophage, which is a state integrated into the bacterial genome or plasmid. Moreover, for example, in the bacteria identification method in the present embodiment, phagemid can be introduced into cells by any method such as using electroporation and nanoparticles.

Further, in the bacterial identification method of the present embodiment, detection may be performed that does not necessarily require suppression of bacterial growth or complete lysis. In such case, for example, CAS13a binds to generate non-specific RNA-degrading activity, and RNA bound to various fluorescent probes is cleaved. Thereby, various reporters such as fluorescence may be induced to detect the presence or absence, the copy number, the expression level, or the like, about the specific gene. Even in this case, when detected by the bacterium identification method of the present embodiment, the detected bacterium can be an antibacterial target. That is, the antibacterial phage of the present embodiment can be used for antibacterial applications.

In addition, the antibacterial phage according to the first embodiment and the second embodiment of the present invention can be used in combination with other compositions, and the like. Furthermore, it is also possible to provide it as a "cocktail" including a plurality of types of antibacterial phages. Further, the composition of the present invention may be administered, sprayed, applied, or the like, at the same time as other compositions.

Example 1

Hereinafter, the killing (bacteria elimination) and bacterial identification method by using antibacterial phage according to the first embodiment of the present invention is described more specifically as examples based on specific experiments. However, this embodiment is merely an example, and the present invention is not limited thereto.

[Bactericidal Effect of Bacteria Having a Specific Gene of CRISPR-Cas13a]

(Preparation of Tetracycline-Induced $Bla_{IMP}$-1 Expression Vector)

The sequence of tetracycline-dependent expression control region is amplified from pC008 (obtained from Dr. F. Zhang) with primers of TetReg SalI-f, "ATATGTCGACGCATGCTTAAGACCCACTTTC" and TetReg BamHI-r, "ATATGGATCCTTTCTCCTCTTTAGATCTTTTG." It was subcloned into the SalI-BamHI site of the pSP72 vector (hereinafter referred to as "pSP72 aTc-inducible vector"). Then, the sequence of $bla_{IMP-1}$ (carbapenem resistance gene) was amplified from multidrug-resistant colorectal cocci by using primers of IMP-1 clo BamHI-f, "ATATGGATCC ATGAGCAAGTTATCTGTATTC" and IMP-1 clo EcoRI-1, "ATATGAATTCTTAGTTGCTTGGTTTTGATG", and it was cloned into the BamHI-EcoRI site of the pSP72 aTc-inducible vector ("pSP72 aTc-inducible IMP-1 vector", hereinafter referred to as "tetracycline-inducible $bla_{IMP-1}$ expression vector").

(Preparation of CRISPR-Cas13a Expression Vector Targeting the $Bla_{IMP-1}$ Gene)

CRISPR-Cas13a expression vector, pC003 (provided by Dr. F. Zhang), was amplified with pC003 PCR-r, "CCAGCTGTTAAACGAGCTTTAATGCGGTAGTTTATC", and pC003 PCR-f, "GAAGGGGACTAAAACGGAGACCGAGATTGGTCTCG", the regions of Cas13a, Cas1, and Cas2 were also amplified by LsCas13a clo-f, "TCGTTTAACAGCTGGGAAAATG", LsCas13a clo-r, "GTTTTAGTCCCCTTCGATATTGG" from the genomic DNA of Lepttrikia shahii (DSM 1975), two DNA fragments were bound by In-Fusion HD Cloning Kit (hereinafter, this is referred to as "pKLC5 vector"), the pKLC5 vector was cleaved with a BsaI restriction enzyme, and the crRNA sequence targeting $bla_{IMP-1}$ was inserted. The target sequence is "ATGTTCATACTTCGTTTGAAGAAGTTAA" (complementary sequence) corresponding to SEQ ID NO: 17 in the sequence listing, and it is a region of 104 to 131 bases after the start of translation of $bla_{IMP-1}$. Two oligo DNAs ("tatccATGTTCATACTTCGTTTGAAGAAGTTAA", "aaacTTAACTTCTTCAAACGAAGTATGAACATg") were synthesized, annealed, and inserted into the BsaI site of pKLC5 ("pKLC5 BsaI IMP-1_104 vector", and hereinafter, referred to as "CRISPR-Cas13a expression vector").

(the Bactericidal Effect of the CRISPR-Cas13a Plasmid on Bacteria Having a Specific Gene)

As refer to FIG. 2, the results were described by culturing the above-mentioned *E. coli* by transforming each plasmid of CRISPR-Cas13a of this example, transforming it, and culturing it. *E. coli* DH5-alpha strain was transformed with a tetracycline-induced $bla_{IMP-1}$ expression vector (ampicillin resistance, ColE1 ori). This *E. coli* was further transformed with a CRISPR-Cas13a expression vector (chloramphenicol resistance, p15A ori) targeting the $bla_{IMP-1}$ gene. The obtained *E. coli* was cultured in LB liquid medium (ampicillin, chloramphenicol) at 37 degree C. for 12 hours, and then OD650 was adjusted to 0.02 in LB liquid medium (ampicillin, chloramphenicol). After shaking culture at 37 degree C. for 1 hour, ice tetracycline was added to a final concentration of 100 ng/ml to induce the expression of the $bla_{IMP-1}$ gene.

FIG. 2A shows the series of *E. coli* in which the experiment was conducted. Series 1, 2 and 4 show experimental examples of control, and series 3 shows experimental examples in which all are introduced. In the experimental item "$bla_{IMP-1}$ sequence", "−" is *E. coli* into which only "pSP72 aTc-inducible vector" was introduced, and "+" was indicates *E. coli* into which the tetracycline-inducible $bla_{IMP-1}$ expression vector was also introduced. The "$bla_{IMP-1}$ sequence recognized by CRISPR" indicates that "−" is *E. coli* into which only pKLC5 has been introduced, and "+" is *E. coli* into which "CRISPR-Cas13a expression vector" has been introduced.

Figure 2B:
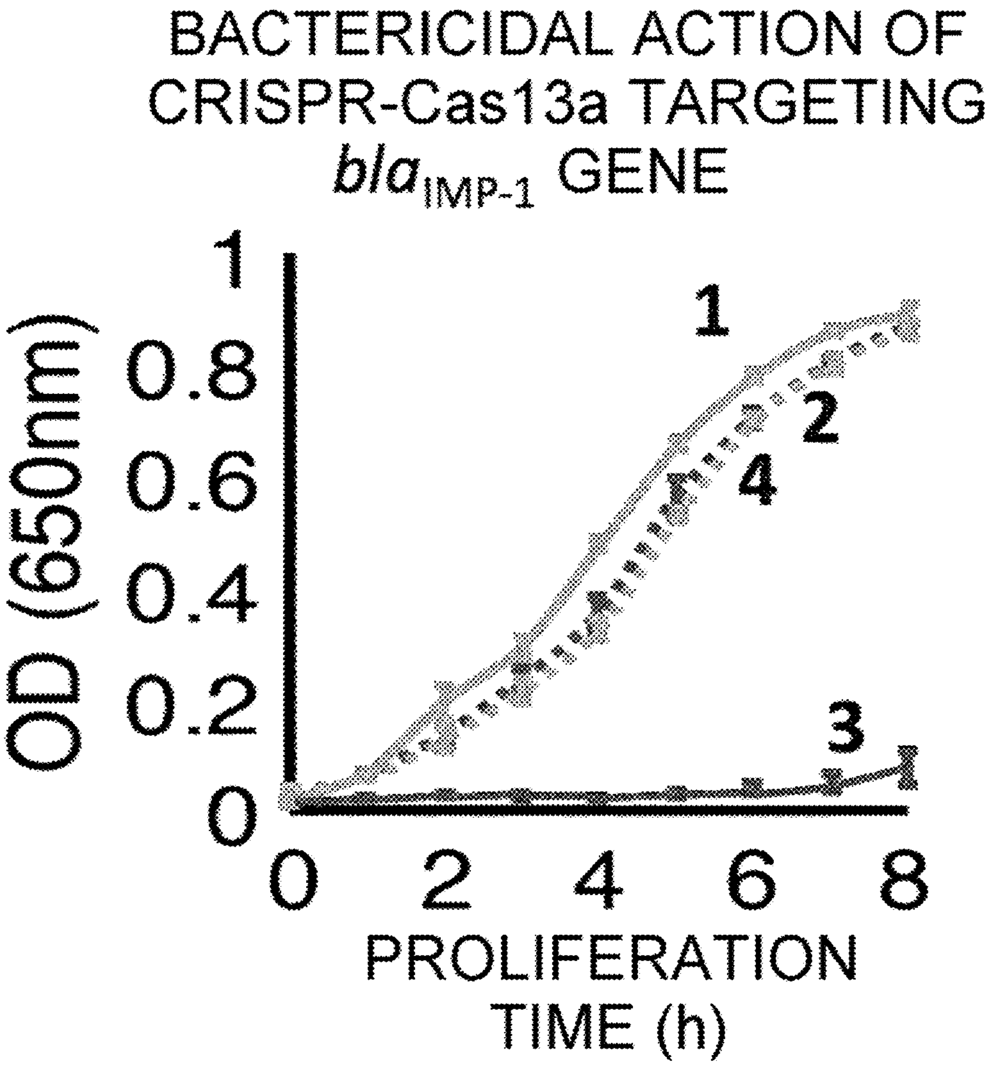

FIG. 2B is a graph showing the results of measuring OD650 over time. The horizontal axis represents the growth time (h) after the addition of ice tetracycline, and the vertical axis represents OD (650 nm).

Figure 2C:
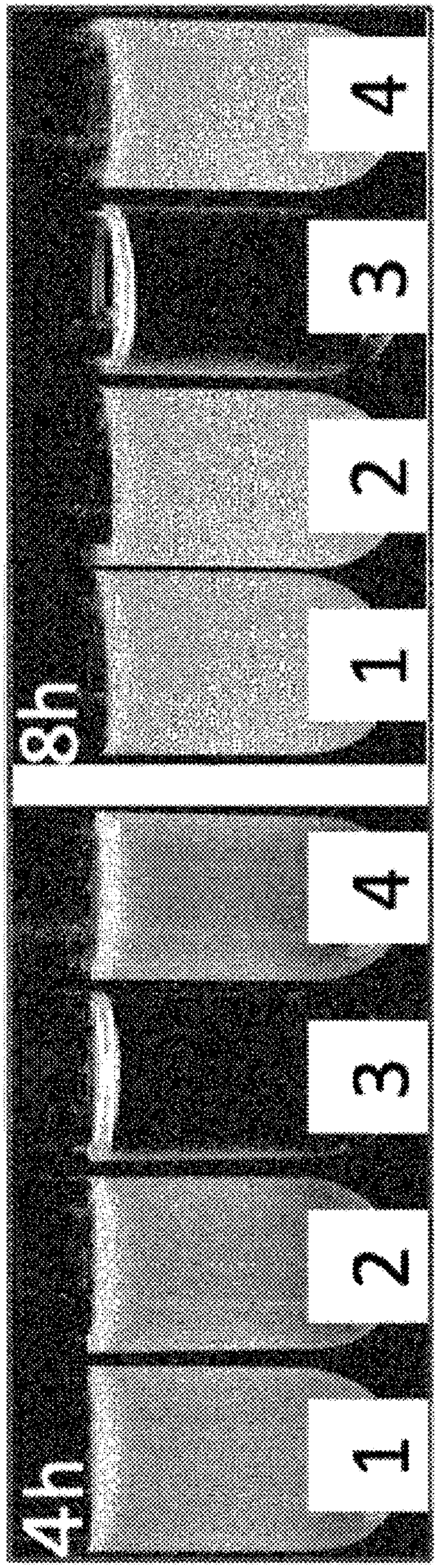

FIG. 2C shows photographs of *E. coli* cultured in vitro after 4 hours (4 h) and 8 hours (8 h).

As shown in these results, CRISPR-Cas13a designed to recognize the $bla_{IMP-1}$ gene as a target suppressed the growth of *E. coli* having the target specific gene $bla_{IMP-1}$. That is, it was confirmed that the designed CRISPR-Cas13a has a sequence-specific bactericidal effect on *E. coli* having the specific gene.

[Bactericidal Effect of Antibacterial Phage on Bacteria Having a Specific Gene]

Next, the designed CRISPR-Cas13a was mounted on a phage to verify the bactericidal effect on *E. coli* having a specific gene.

Figure 3:
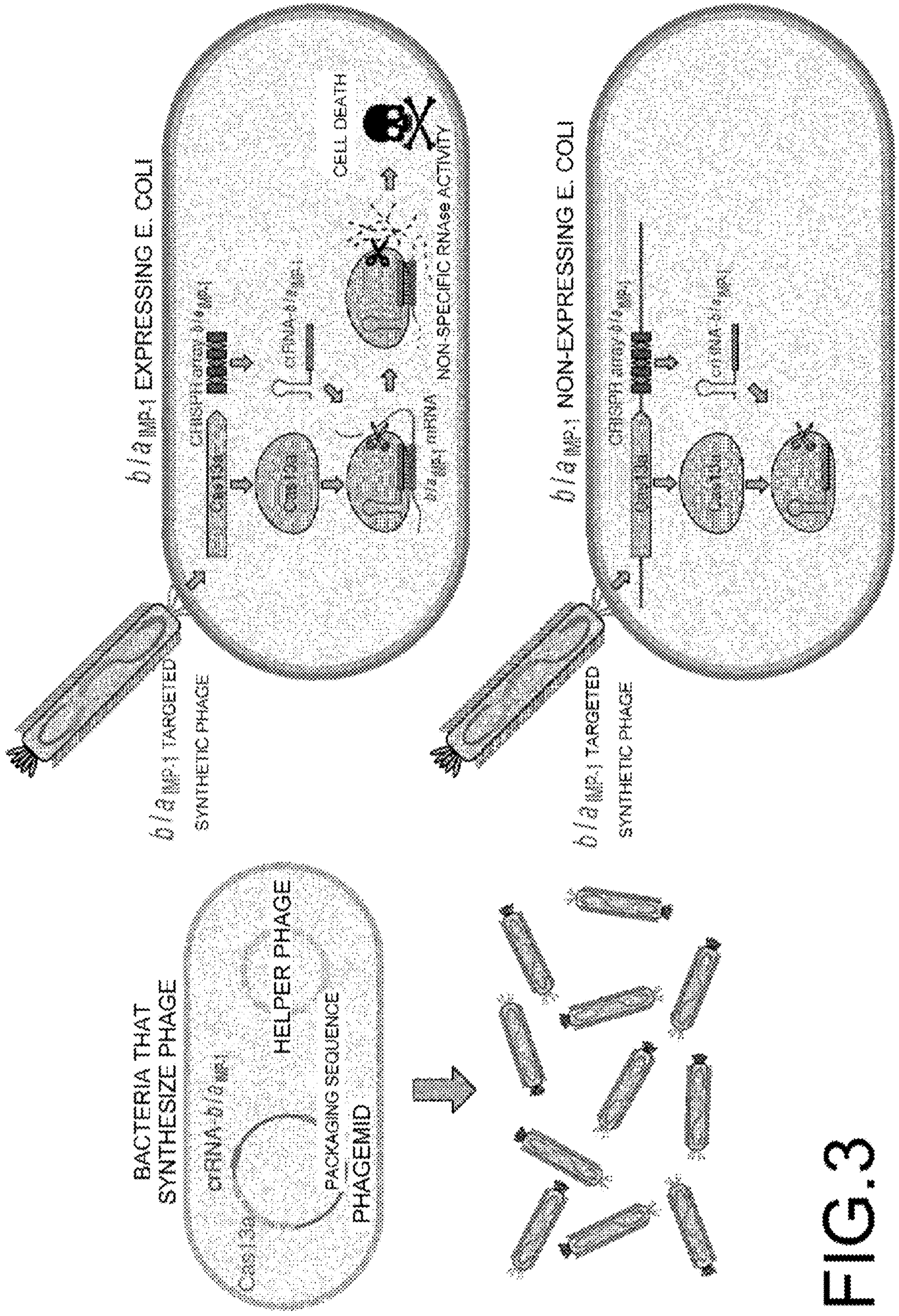
FIG. 3 is a conceptual diagram of synthesis and experiment of the antibacterial phage according to Example 1 of the present invention.

FIG. 3 shows a conceptual diagram of the synthesis of antibacterial phage, which is a synthetic phage carrying CRISPR-Cas13a targeting the $bla_{IMP-1}$ gene, and a conceptual diagram of the reaction when infected with the synthetic phage. Specifically, the phagemid and helper phage as described later are introduced into the phage-synthesizing bacterium and packaged, and thereby the antibacterial phage including CRISPR-Cas13a having a target sequence (hereinafter referred to as "$bla_{IMP-1}$ targeted synthetic phage") is prepared. This $bla_{IMP-1}$ targeted synthetic phage selectively kills *E. coli* expressing $bla_{IMP-1}$. On the other hand, the $bla_{IMP-1}$ targeted synthetic phage does not kill *E. coli* that does not express $bla_{IMP-1}$.

(Preparation of CRISPR-Cas13a Expression Vector Targeting $Bla_{IMP-1}$)

The expression vector pKLC5 BsaI IMP-1_104 described above was improved as follows. Cas1/2 present on the vector was deleted because it does not participate in the bactericidal activity by Cas13a. This deletion is performed by performing PCR of vector Cas1Cas2 the with del SacI-f, "ATATGAGCTCATGGGAGAAAAAATTTCACAAAAC" and Cas1Cas2 del SacI-r, "ATATGAGCTCTCATTCTTATAACGTATCATTCG", after cleaving with SalI restriction enzyme, ligating with "Ligation high ver. 2" (manufactured by TOYOBO). Further, a work was carried out to confer f1 ori and kanamycin resistance to this vector. Specifically, as this vector was used as a template, PCR is performed with the primers, InF13 PCR SalI-f, "tcttcaccctgtcgatgggaaaatgtggaatttg", InF13 PCR SmaI-r, "caggatcttctgcccaattaggctctagttagcct", then, f1 ori and kanamycin resistance of pRC319 (obtained from Dr. Timothy Lu) were amplified with InF13 pRC319-f, "gggcagaagatcctgcagg", InF13 pRC319-r, "tcgacagggtgaagacgaaag", and two DNA fragments were bound by In-Fusion HD Cloning Kit (Hereinafter, this is referred to as "pKLC21 BsaI IMP-1_104 vector").

Further, as a control, a control vector obtained by similarly improving the expression vector pKLC5 was also prepared.

(Preparation of M13 Helper Phage Plasmid)

The helper phage M13KO7 (manufactured by NEB biolabs) was infected with *E. coli* NEB5-alpha F'I$^q$ strain (manufactured by NEB biolabs), and the plasmid was recovered. The f1 origin sequence of M13KO7 was deleted to prevent self-packaging. By using the M13KO7 plasmid as a template, PCR was performed by using the primers of M13KO7 PCR In-Fusion-f, "cctattggttaaaaaatgagctg" and M13KO7 PCR In-Fusion-r, "actatggttgctttgacgag".

Further, p15A ori and chloramphenicol resistance gene of pBAD33 vector were amplified by pBAD33 PCR In-Fusion-f, "caaagcaaccatagtgtagcaccaggcgtttaagg" and pBAD33 PCR In-Fusion-r, "tttttaaccaataggcatcaccgatggggaagatc", and two amplified samples were combined with In-Fusion HD Cloning Kit (manufactured by TakaRa Bio) (hereinafter referred to as "pKLC25 vector").

(Preparation of $Bla_{IMP-1}$ Expressing *E. coli* (*E. coli* Targeted by Antibacterial Phage))

To delete the extra sequence (f1 ori) of the pBAD33 vector, the pBAD33 vector was amplified with two primers, pBAD33 PCR XhoI-f, "tcaCTCGAGcgaatttgctttcgaatttc" and pBAD33 PCR XhoI-r, "tcaCTCGAGcaaaagagtttgtagaaacgc", after cleavage with the restriction enzyme XhoI, it was ligated by "Ligation high ver. 2" (hereinafter referred to as "pKLC23 vector"). The pKLC23 was amplified with two primers, pKLC23 PCR In-Fusion-f2, "GAATTCgatcctctagagtc" and pKLC23 PCR In-Fusion-r2, "tgcttcgtccatttgacag". Further, from the sequence of the native $bla_{IMP-1}$ promoter sequence (artificial synthesis, manufactured by genewiz, GenBank ID: AB733642, 716 bp to 1168 bp), a part was amplified with Intl1 pro In-Fusion-f, "caaatggacgaagcaTGACGCACACCGTGGAAAC" and Intl1 pro In-Fusion-r, "tagaggatcGAATTCGAGAATGGATTTTGTGATGC". Then, two DNA fragments were bound by In-Fusion HD Cloning Kit (pKLC26 vector). The $bla_{IMP-1}$ sequence is performed PCR amplification by using IMP-1 In-Fusion-f, "ACAAAATCCATTCTCATGAGCAAGTTATCTGTATTC" and IMP-1 In-Fusion-r, "tagaggatcGAATTCTTAGTTGCTTGGTTTTGATG", further, pKLC26 is used as a template, an amplified DNA fragment with primers of pKLC26 In-Fusion-f, "GAATTCgatcctctagagtc" and pKLC26 In-Fusion-r, "GAGAATGGATTTTGTGATGC" was prepared. The two DNA fragments were ligated by In-Fusion HD Cloning Kit (hereinafter referred to as "pKLC26 IMP-1 vector"). The *E. coli* NEB5-alpha F'I$^a$ strain transformed with this pKLC26 IMP-1 vector ($bla_{IMP-1}$ expressing *E. coli*) and *E. coli* NEB5-alpha F'I$^a$ strain for control without transformation ($bla_{IMP-1}$ non-expressing *E. coli*) were prepared.

(Preparation of $Bla_{IMP-1}$ Targeted Synthetic Phage)

Cas13a-loaded M13 phage (phagemid) targeting $bla_{IMP-1}$ Was generated. Specifically, the helper phage synthesis plasmid pKLC25 was transformed into *E. coli* MC1061 (phage synthesizing bacterium) and selected by chloramphenicol. This *E. coli* was transformed with a CRISPR-Cas13a expression vector (pKLC21 BsaI IMP-1_104 vector) targeting $bla_{IMP-1}$ and was selected with chloramphenicol+kanamycin. The colonies were seismic cultured in LB liquid medium (chloramphenicol+kanamycin) at 37 degree C. until *E. coli* were sufficiently increased. After centrifugation at 8,000×g for 20 minutes, the supernatant was passed through a 0.22 micro-m filter. Add the same amount of PEG buffer (5 mM Tris-HCl (pH 7.5), 10% PEG6000, 1M NaCl (58 g/L), 5 mM $MgSO_4 \cdot 7H_2O$ (1.23 g/L)), after mixing well, it was left at 4 degree C. for 1 hour. Centrifuge at 4 degree C. with 12,000×g for 10 minutes to make pellets of antibacterial phage, eliminated the supernatant as much as possible, and then suspended in SM Buffer (50 mM Tris-HCl pH7.5, 0.1M NaCl, 7 mM $MgSO_4 \cdot 7H_2O$, 0.01% gelatin). This was used as a solution of $bla_{IMP-1}$ targeted synthetic phage.

Also, the control vector was also transformed in the same manner to prepare a solution of $bla_{IMP-1}$ non-target synthetic phage.

(Measurement of TFU (Transduced Colonies Forming Unit))

These antibacterial phages (M13 phage carrying Cas13a) were diluted 1000-fold with SM Buffer. 1 ml of *E. coli* NEB5-alpha F'I$^q$ strain was previously liquid-cultured, and when the OD600 reached about 0.1, 10 micro-l of diluted antibacterial phage was added and the mixture was shaken at 37 degree C. for 30 minutes. 100 micro-l of the bacterial solution was plated on an LB plate, an LB plate (containing chloramphenicol), and an LB plate (containing kanamycin). Then, they were incubated overnight at 37 degree C., after confirming that there was no *E. coli* on the LB plate (containing chloramphenicol), the number of colonies growing on the LB plate (containing kanamycin) was counted, and the TFU was calculated.

(Phagemid Induction Assay)

The phagemid (M13 phage carrying Cas13a) on which TFU was measured was serially diluted 10-fold. When the pre-cultured *E. coli* NEB5-alpha F'I$^q$ strain reaches about OD600=0.5, 100 micro-l of the bacterial solution and 3 mL of the LB solution (0.5% agarose) warmed to 50 degrees were mixed and poured into an LB plate. After the LB plate had hardened, 2 micro-l of each of the serially diluted antibacterial phage solution was added from above the plate and cultured at 37 degree C.

Figure 4:
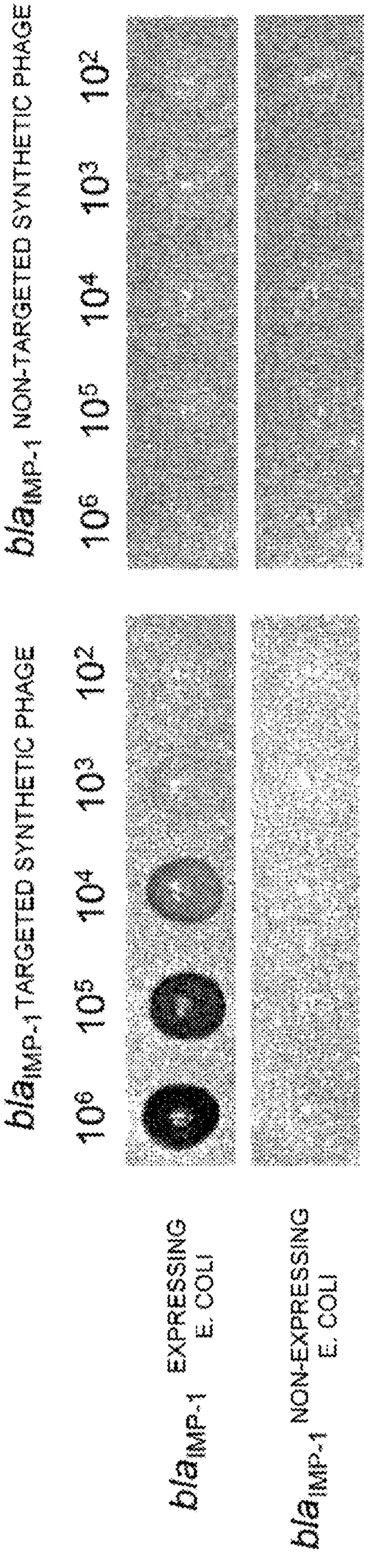
FIG. 4 is a photograph showing a bactericidal effect of bacteria by the antibacterial phage infection according to Example 1 of the present invention.

In FIG. 4, a solution of blamMP-1 targeted synthetic phage or $bla_{IMP\text{-}1}$ non-targeted synthetic phage was added to $bla_{IMP\text{-}1}$ expressing *E. coli* or $bla_{IMP\text{-}1}$ non-expressing *E. coli* at different concentrations. The result of whether or not it was lysed is shown. As a result, the $bla_{IMP\text{-}1}$ targeted synthetic phage selectively killed *E. coli* expressing $bla_{IMP\text{-}1}$. That is, sequence-specific antibacterial activity was confirmed. In addition, the $bla_{IMP\text{-}1}$ targeted synthetic phage showed a bactericidal effect even in a 1000-fold diluted solution.

[Bacterial Identification by Using Phage Carrying CRISPR-Cas13a]

Next, we experimented with a bacteria identification method that can easily detect the bacteria where CRISPR-Cas13a is designed to target a specific gene to produce antibacterial phage loaded on M13 phage, and bacteria having the specific gene are selectively sterilized. The following is an example of the experiment. In this example, the resistance gene was targeted.

(Inhibition of Growth of Specific Gene-Carrying *E. coli* by Cas13a)

Figure 5:
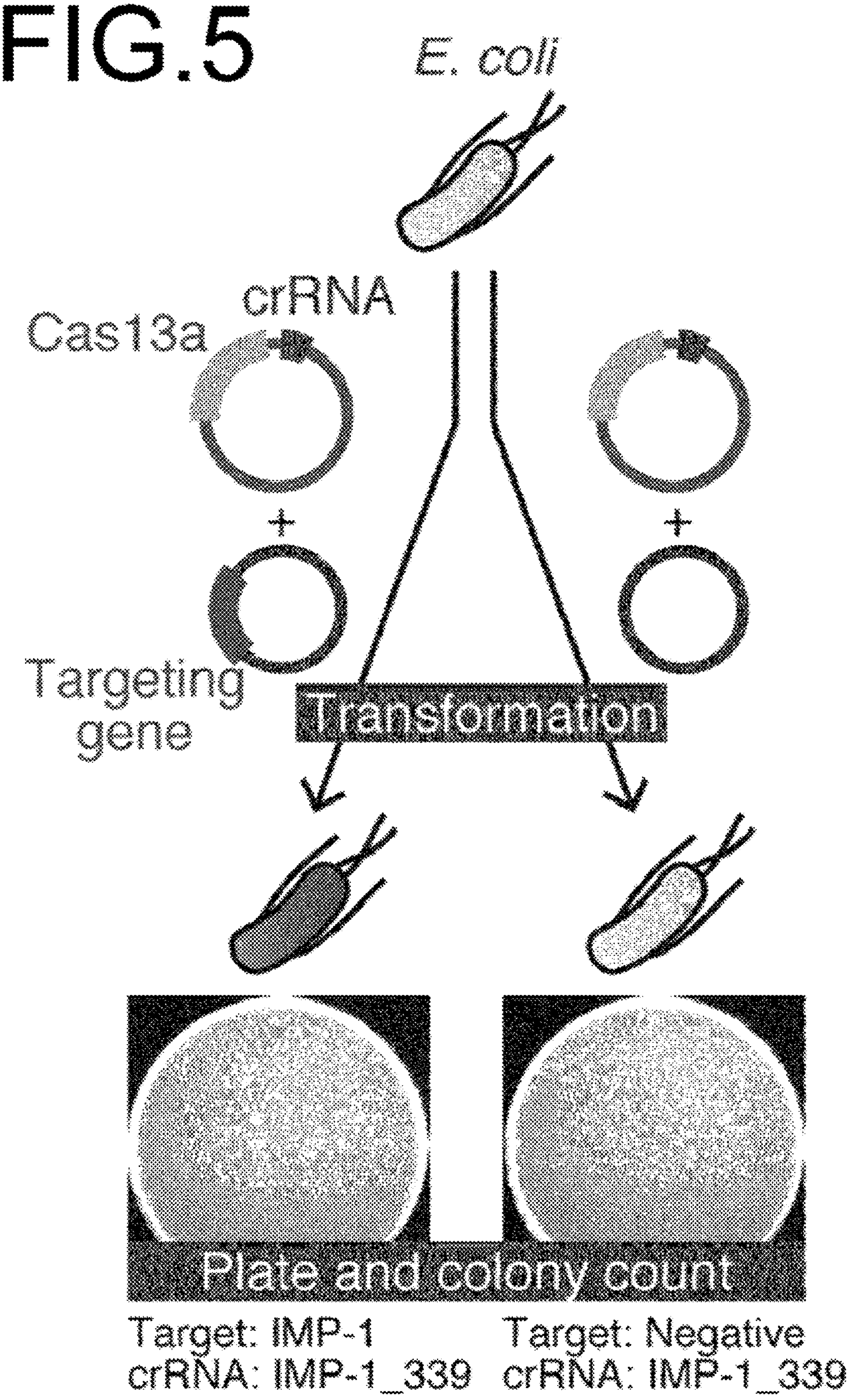
FIG. 5 is a diagram and a photograph showing growth suppression of specific gene-carrying *E. coli* by the antibacterial phage infection according to Example 1 of the present invention.

FIG. 5 shows an example of suppressing the growth of *E. coli* carrying a specific gene. *E. coli* strain MC1061 (manufactured by Lucigen, Inc.) was simultaneously transformed with i) a plasmid expressing Cas13a and crRNA and ii) a plasmid expressing a specific gene of crRNA (a plasmid expressing a targeting gene). The plasmid of i) carries the kanamycin resistance gene, and the plasmid of ii) carries the chloramphenicol resistance gene. Transformed MC1061 was cultured on an LB plate (containing kanamycin and chloramphenicol), and a photograph of the plate was taken 12 hours later. When Cas13a and crRNA that recognizes the 339th base of IMP-1 was expressed in *E. coli* expressing IMP-1, the growth of *E. coli* was suppressed.

Preliminary experiments have shown that the bactericidal effect of CRISPR-Cas13a depends largely on the sequence structure of a particular gene. Therefore, the specificity (order) of the specific gene sequence of CRISPR-Cas13a was examined, and the optimum sequence was extracted. That is, in this example, the specific gene sequence of CRISPR-Cas13a was optimized.

In this example, with reference to the paper of CRISPR-Cas of Non-Patent Document 1, 3 to 8 base sequences for each specific gene were examined as the base sequence of the target site.

Specifically, target sequences of CRISPR-Cas13a were designed for 10 types of drug resistance genes. As these 10 kinds of genes, sequences of IMP-1 (GenBank ID: S71932), KPC-2 (AY034847), NDM-1 (FN396876), OXA-48 (AY236073), VIM-2 (AF191564), mcr-1 (KP347127), mcr-2 (LT598652), mcr-3 (KY924928), mcr-4 (MF543359), and mcr-5 (KY807921), are used. In addition, an RFP (Red Fluorescent Protein, GenBank ID: KJ021042) sequence was used as a control. Table 3 below shows the relationship between the SEQ ID NO: (No.) in the sequence listing, the name of the sequence mainly targeting the drug resistance gene (spacer name), and the selected target site base sequence (target sequence, spacer sequence).

TABLE 3

| No | Spacer name | Spacer sequence |
|---|---|---|
| 1 | RFP | CGGTCTGGGTACCTTCGTACGGACGACCTTC |
| 2 | mcr-1_47 | AAAACGGCAACACTCGCCACAAGAACAA |
| 3 | mcr-1_1021 | CGGATTTATAATCGGCAAATTGCGCTTT |
| 4 | mcr-1_1495 | CCATTGGCGTGATGCCAGTTTGCTTATC |
| 5 | mcr-2_37 | CCACCAAACCCATCAGCACAAAAGGATT |
| 6 | mcr-2_1015 | CTGATTTATAATCAAAATACTGCGTGGC |
| 7 | mcr-2_1487 | GCAGTTGGCTTGAATGTCGTATTATTTG |
| 8 | mcr-3_34 | CAAAATACAGTGCCAAAAAGAACATAAG |
| 9 | mcr-3_997 | GGTGATCCTTTGGTTCGATTTCGATGTT |
| 10 | mcr-3_1436 | GTAAATCCAGGTGACATCCACACCTGCA |
| 11 | mcr-4_41 | GCAACATAAAACAACGCAGTGATGAAAG |
| 12 | mcr-4_1000 | GATCACTCTTCAAATCTATCGTGAGATT |
| 13 | mcr-4_1442 | CTAAAGTCATTAGATACCCAAGCCAGCA |
| 14 | mcr-5_50 | CTGATGAACAGAGTCAAAAATTCAGTGC |
| 15 | mcr-5_1024 | GATGGCCTGCCGAAGACAGGTTTTCAAA |
| 16 | mcr-5_1462 | CATAAACCTGACTCGACTGCCACCAGAT |
| 17 | IMP-1_104 | TTAACTTCTTCAAACGAAGTATGAACAT |
| 18 | IMP-1_291 | CCACTCTATTCCGCCCGTGCTGTCGCTA |
| 19 | IMP-1_298 | AATTAAGCCACTCTATTCCGCCCGTGCT |
| 20 | IMP-1_300 | AGAATTAAGCCACTCTATTCCGCCCGTG |
| 21 | IMP-1_331 | TTAATTCAGATGCATACGTGGGGATAGA |
| 22 | IMP-1_339 | TTCATTTGTTAATTCAGATGCATACGTG |
| 23 | IMP-1_436 | GGCCTGGATAAAAAACTTCAATTTTATT |
| 24 | IMP-1_615 | ACTTGGAACAACCAGTTTTGCCTTACCA |
| 25 | NDM-1_117 | ATCGCCAAACCGTTGGTCGCCAGTTTCC |
| 26 | NDM-1_406 | ACAACGCATTGGCATAAGTCGCAATCCC |
| 27 | NDM-1_724 | AATGGCTCATCACGATCATGCTGGCCTT |
| 28 | OXA-48_201 | ATTGGGAATTTTAAAGGTAGATGCGGGT |
| 29 | OXA-48_364 | CAATTTGGCGGGCAAATTCTTGATAAAC |
| 30 | OXA-48_470 | GCCGAAATTCGAATACCACCGTCGAGCC |
| 31 | KPC-2_50 | GTCAGCGCGGTGGCAGAAAAGCCAGCCA |
| 32 | KPC-2_232 | CCTGCTGCTGGCTGCGAGCCAGCACAGC |
| 33 | KPC-2_732 | CCCAGTGGGCCAGACGACGGCATAGTCA |
| 34 | VIM-2_229 | CTGTATCAATCAAAAGCAACTCATCACC |
| 35 | VIM-2_335 | CCGACGCGGTCGTCATGAAAGTGCGTGG |
| 36 | VIM-2_518 | TCGGTCGAATGCGCAGCACCAGGATAGA |

The bactericidal effect of CRISPR-Cas13a was evaluated by designing crRNA against these target site base sequences.

Figure 6:
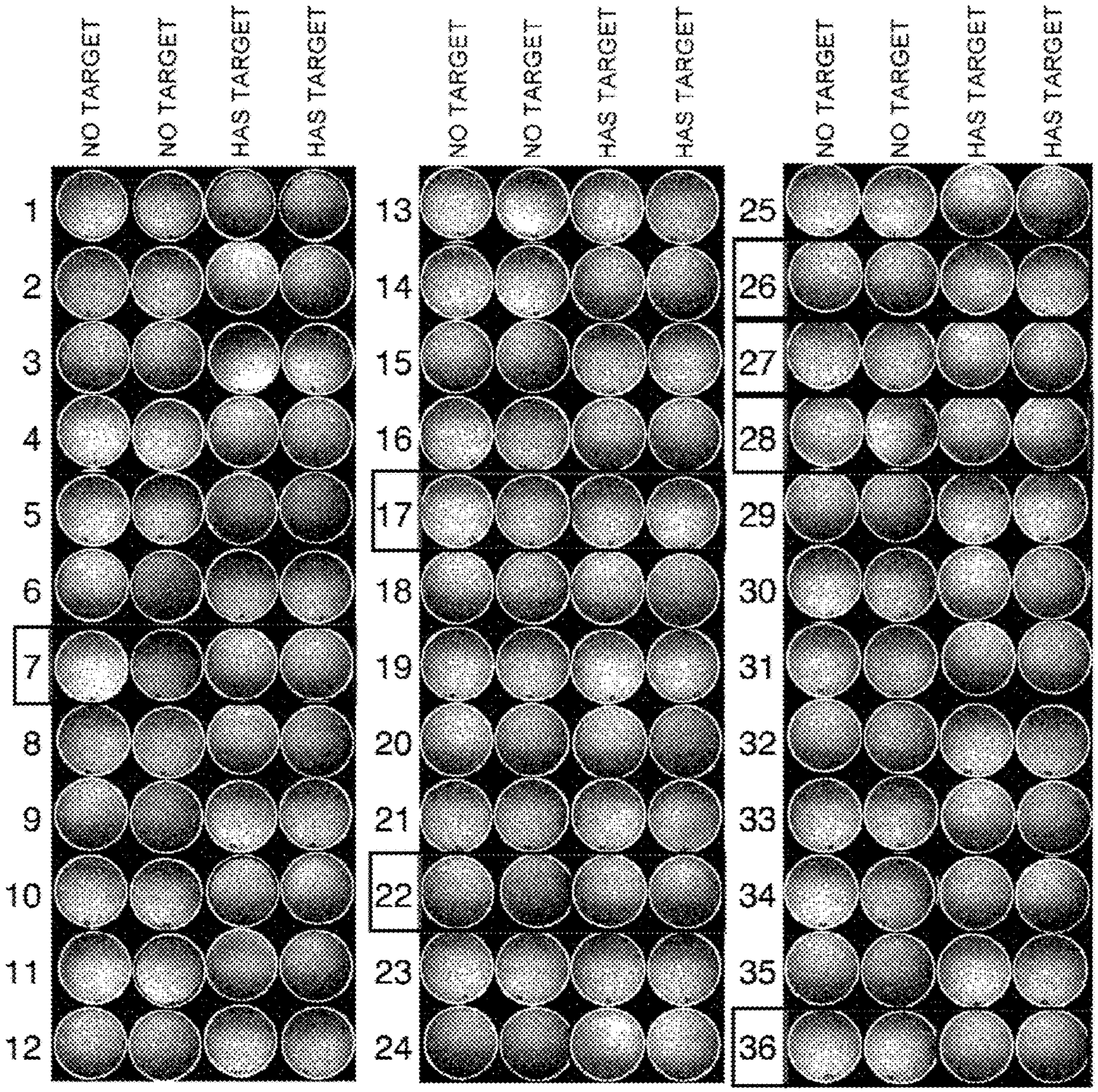
FIG. 6 is a photograph showing the bactericidal activity of each target sequence according to Example 1 of the present invention.

The photograph of FIG. 6 shows the results of designing crRNA for each target sequence in Table 3 and evaluating the bactericidal effect of CRISPR-Cas13a by using it. Specifically, *E. coli* MC1061 was simultaneously transformed with i) Cas13a, a plasmid expressing crRNA corresponding to each target site base sequence, and ii) a plasmid expressing a specific gene of crRNA (with target). The plasmid of i) carries the kanamycin resistance gene, and the plasmid of ii) carries the chloramphenicol resistance gene. FIG. 6 shows a photograph of plates taken of the transformed MC1061 after culturing on LB plates (containing kanamycin and chloramphenicol) cultured at 37 degree C. for 12 hours. About each sequence number, for no crDNA (no target) for the target sequence, from the left, a plate of untransformed (without drug resistance gene) and transformed (with drug resistance gene) are shown. Also, regarding crDNA (with target), from the left, the plates for bacteria without drug resistance genes and bacteria with drug resistance genes are shown. In the plate with the sequence number surrounded by a black frame, in *E. coli* plates with targets and drug resistance genes, almost no colonies appeared, and strong bactericidal activity (growth inhibitory activity) by Cas13a was confirmed. As described above, the bactericidal effect was different depending on the target sequence. Further, strong bactericidal activity (proliferation inhibitory activity) was confirmed when the crDNA having each of SEQ ID NO: 7, SEQ ID NO: 17, SEQ ID NO: 22, SEQ ID NO: 26, SEQ ID NO: 27, SEQ ID NO: 28, and SEQ ID NO: 36 as the target sequence was introduced.

Figure 7:
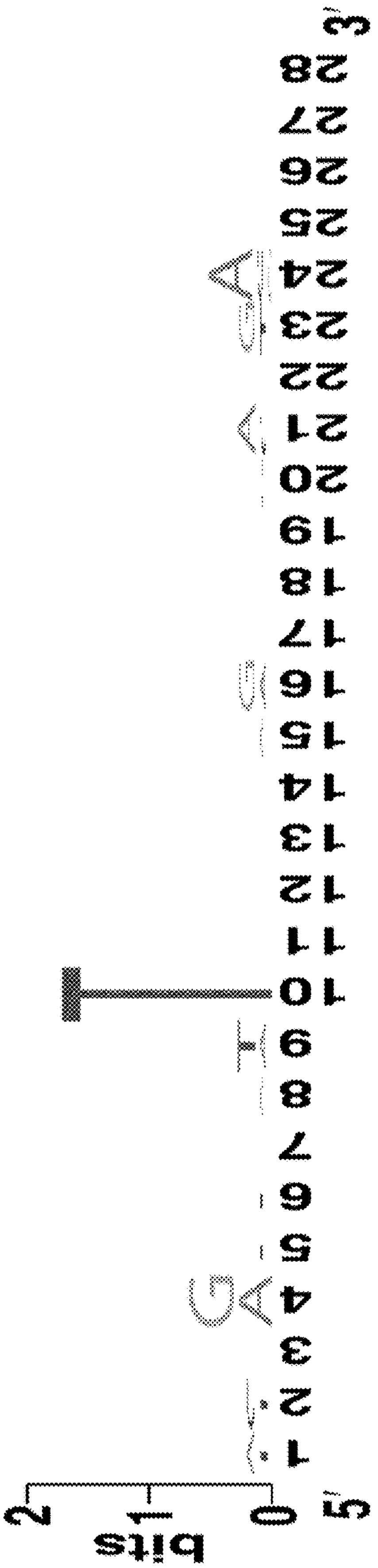
FIG. 7 is a diagram showing the amount of information by the web logo of the target sequence in which strong bactericidal activity according to Example 1 of the present invention was confirmed.

FIG. 7 shows that the target sequences of the sequence numbers for the plates shown in the black frame in FIG. 6 are aligned by Weblogo (URL <https://weblogo.berkeley.edu/>). A bias is seen, as represented by the 10th T. That is, as a result of the examination, in the target sequence designed as a spacer sequence of crRNA of 14 to 28 bases, when the target at the 10th base was T, the bactericidal activity of CRISPR-Cas13a was optimal.

Figure 8:
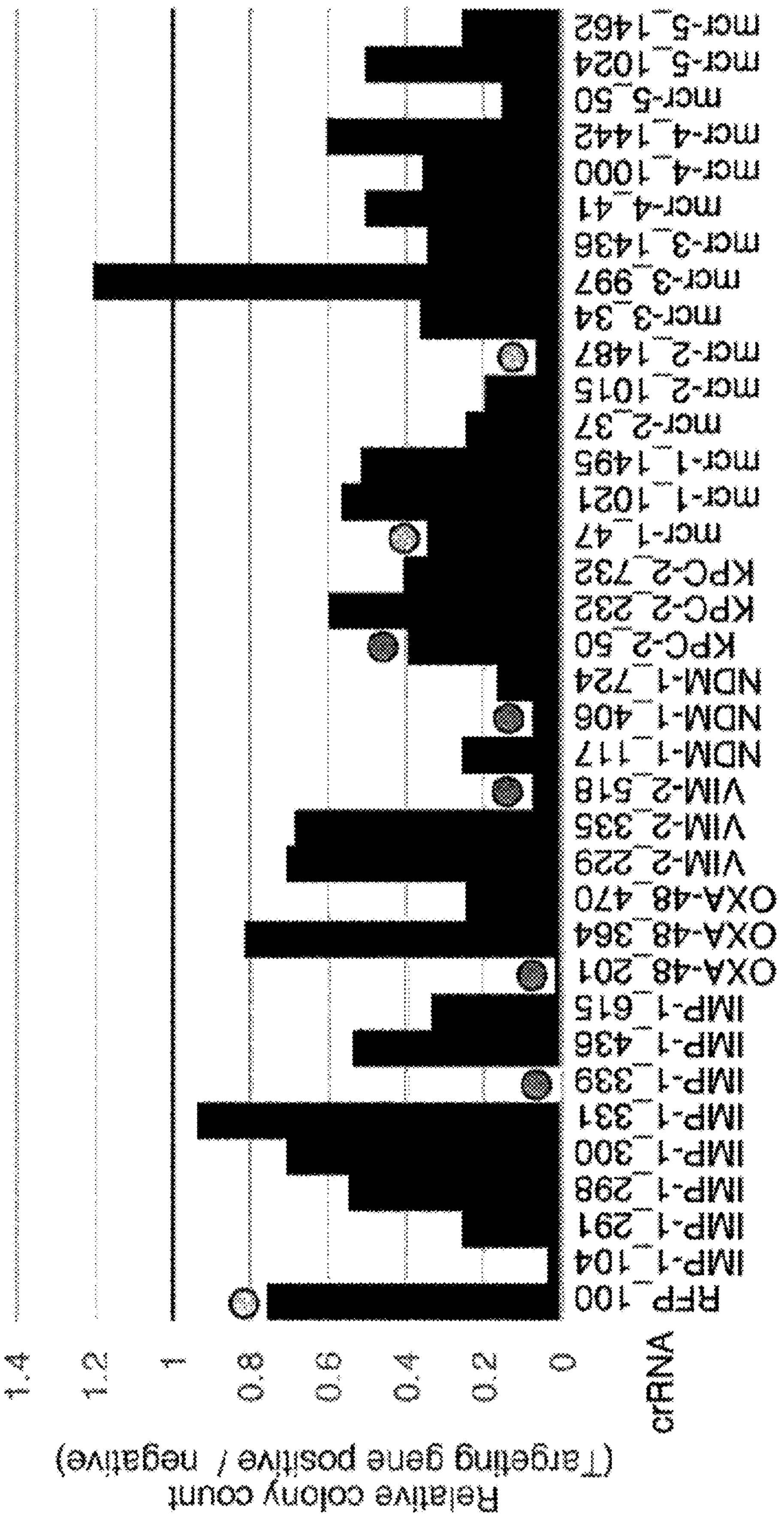
FIG. 8 is a graph counting the number of colonies in the photograph shown in FIG. 6.

FIG. 8 is a graph showing the visually counted number of colonies on the plate of the experiment performed in FIG. 6. However, small colonies are excluded from the count. Here, for each drug resistance gene plate, a relative colony count that the number of colonies on the *E. coli* plate with the drug resistance gene (with the resistance gene) was divided by the number of colonies on the *E. coli* plate without the drug resistance gene (without the resistance gene) was shown. All crRNAs other than mcr-3_997 inhibited the growth of *E. coli* carrying the target drug resistance gene. On this, the part indicated by the circle showed recognizing the above-mentioned strong bactericidal activity and the control RFP (RFP 100). In this way, it is shown that the resistant gene-carrying bacteria can be sterilized efficiently.

(Identification of *E. coli* Carbapenem Resistance Gene by Antibacterial Phage)

Figure 9:
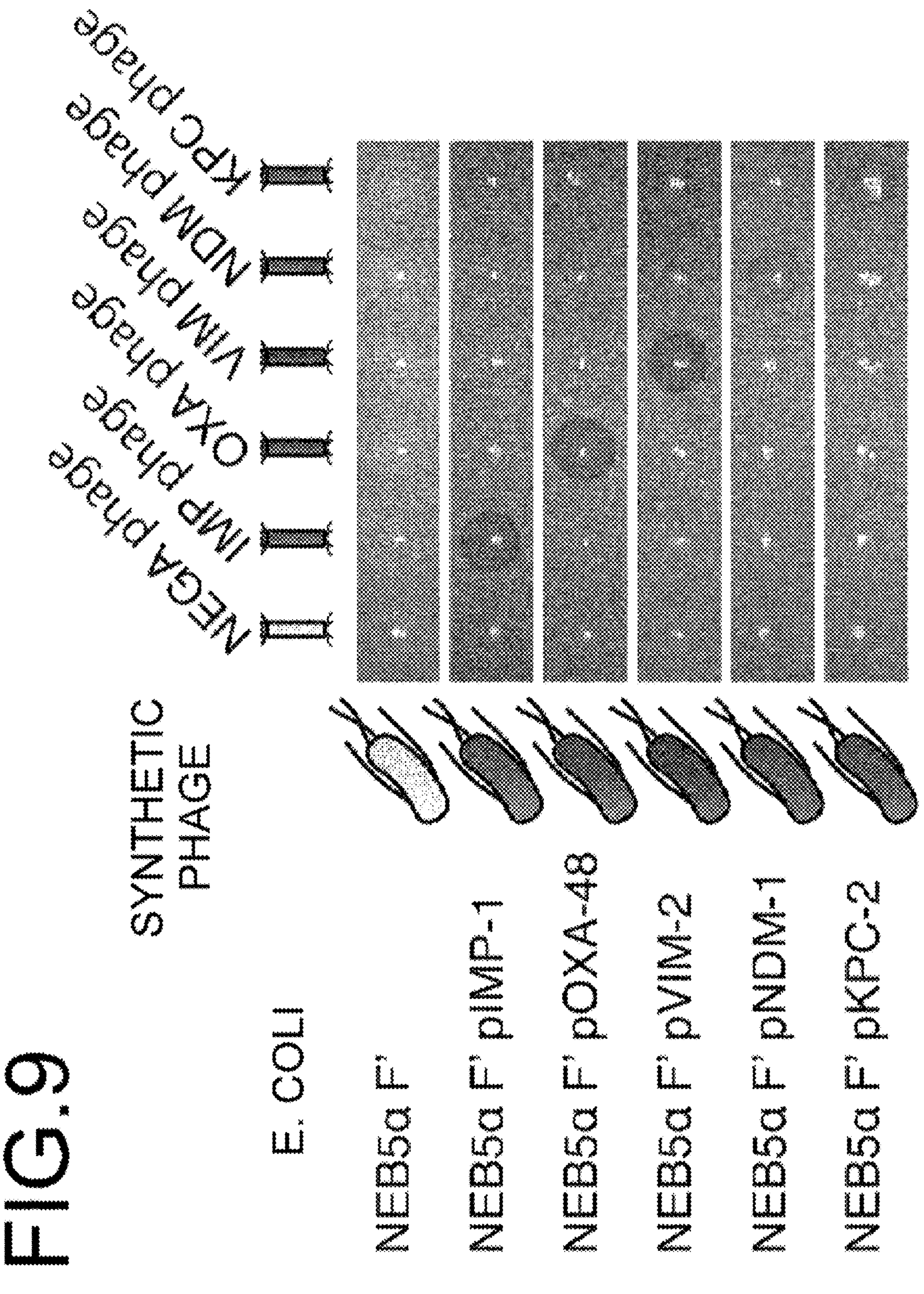
FIG. 9 is a photograph showing a determination result of a carbapenem resistance gene according to Example 1 of the present invention.

FIG. 9 shows the results of identifying the carbapenem resistance gene of *E. coli* with the Cas13a-loaded antibacterial phage. In this experiment, M13 phage was loaded with crRNA and Cas13a for the target sequence in which the above-mentioned strong bactericidal activity was confirmed. *E. coli*, which is the *E. coli* NEB5-alpha F'l$^{q}$ strain, was transformed by using each of plasmids of IMP-1, OXA-48, VIM-2, NDM-1, and KPC-2 for carbapenem resistance genes. The prepared *E. coli* was infected with an antibacterial phage prepared by loading crRNA and Cas13a of each target sequence in the same manner as the above-mentioned bla$_{IMP\text{-}1}$ targeted synthetic phage, incubated on LB soft agar medium without antibiotics, and confirmed that the growth of *E. coli* was inhibited. That is, when *E. coli* having each resistance gene was infected with each antibacterial phage, its growth was suppressed. In this way, it could be used to identify (discriminate) whether *E. coli* had the carbapenem resistance gene.

(Identification of *E. coli* Colistin Resistance Gene by Antibacterial Phage)

Figure 10:
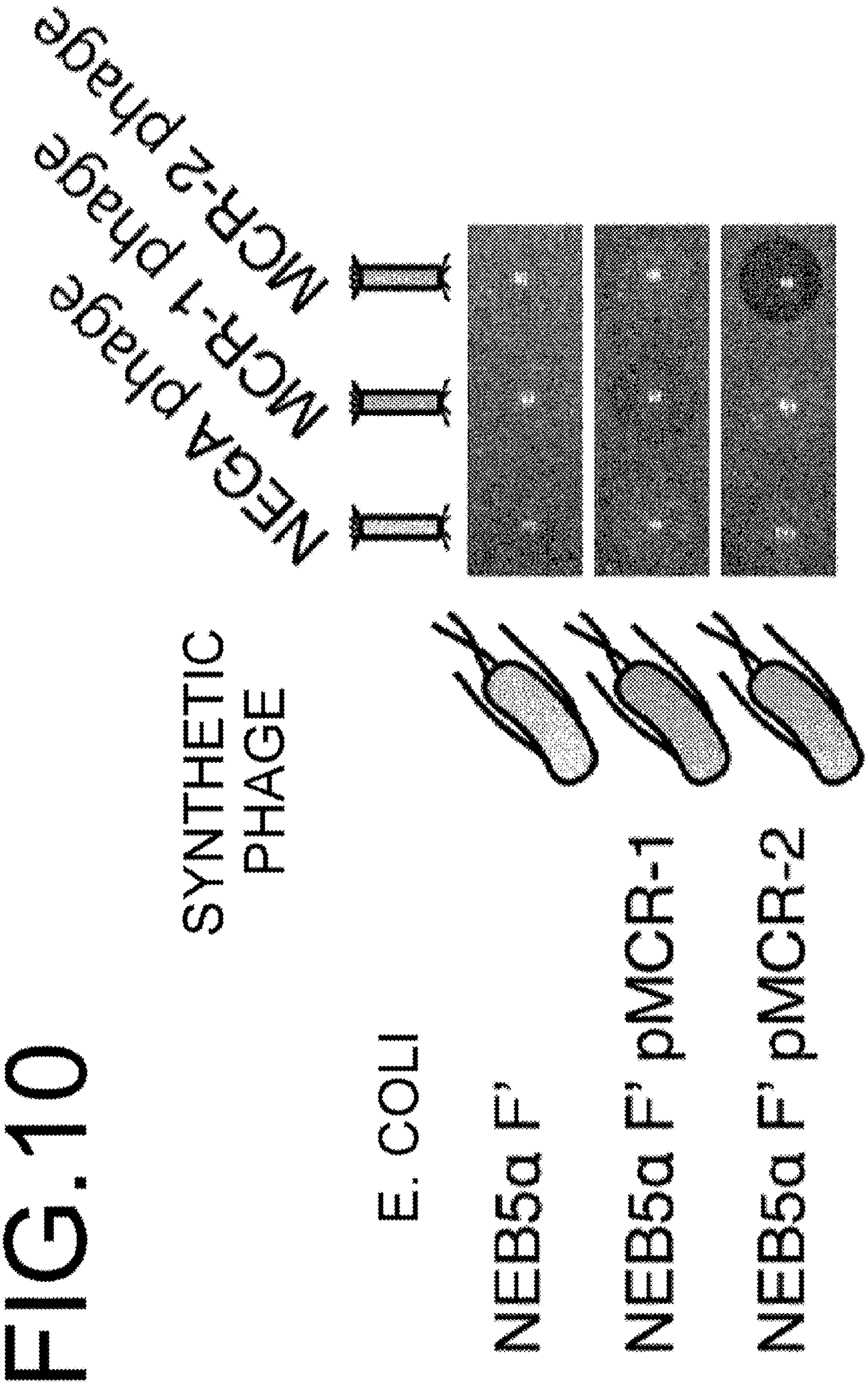
FIG. 10 is a photograph showing a determination result of a colistin resistance gene according to Example 1 of the present invention.

FIG. 10 shows the results of identifying the colistin resistance gene of *E. coli* with the Cas13a-loaded antibacterial phage. In this experiment, M13 phage was loaded with crRNA and Cas13a for the target sequence in which the above-mentioned strong bactericidal activity was confirmed. *E. coli* of NEB 5-alpha F'll$^{q}$ strain was transformed with MCR-1 and MCR-2 plasmids as colistin resistance genes. The prepared *E. coli* was infected with the antibacterial phage prepared in the same manner as described above, incubated on LB soft agar medium without antibiotics, and inhibition of *E. coli* growth was confirmed. Again, it was confirmed that growth was suppressed when each antibacterial phage was infected with *E. coli* having each resistance gene. That is, it was possible to use it for identifying (discriminating) whether *E. coli* carries the colistin resistance gene.

Example 2

(Modification of *E. coli* Flora by Antibacterial Phage)

Figure 11:
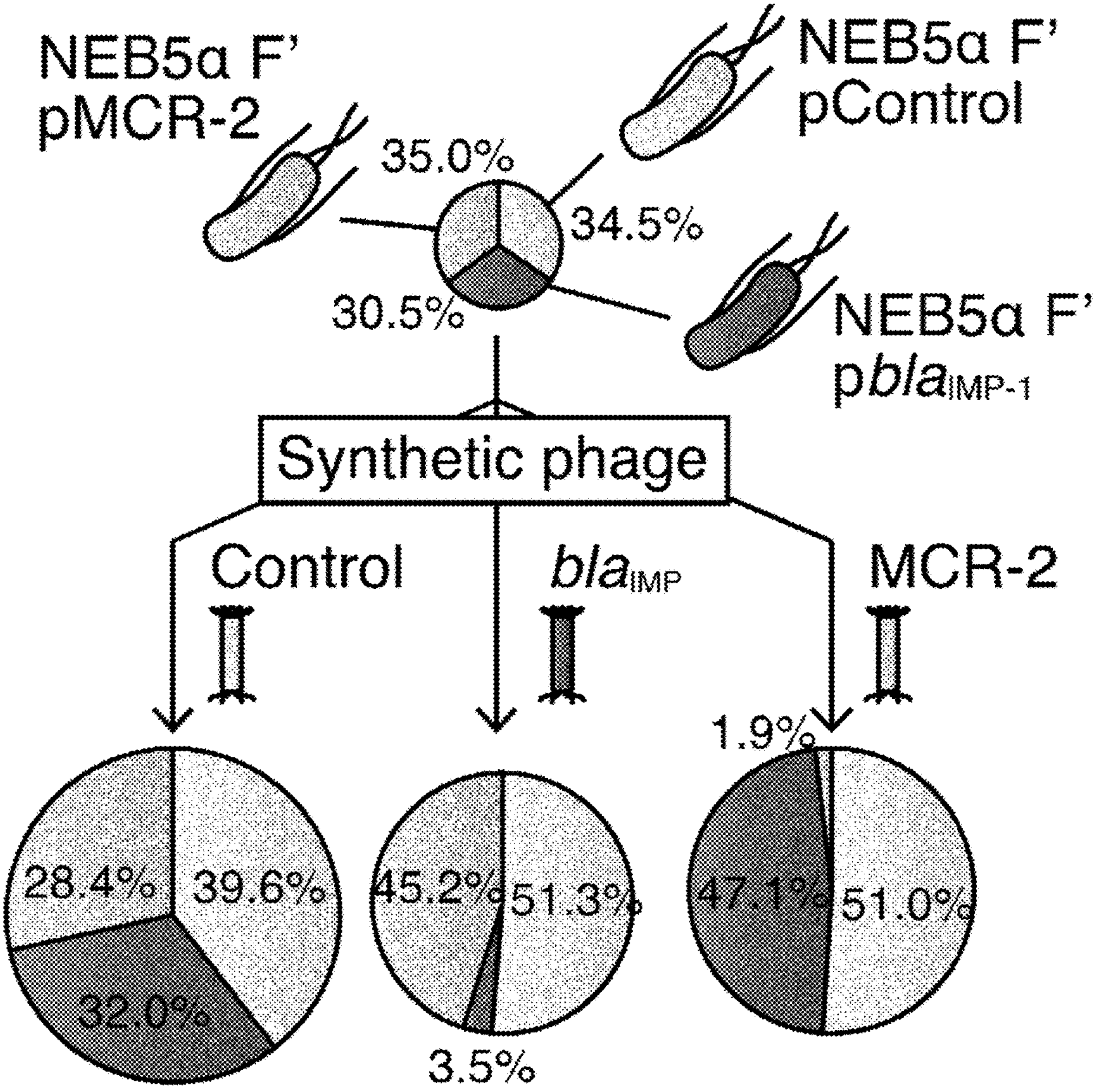
FIG. 11 is a diagram showing the results of bacterial flora modification by antibacterial phage according to Example 2 of the present invention.

FIG. 11 shows the results of selectively eliminating bacteria carrying the carbapenem resistance gene bla$_{IMP\text{-}1}$ and colistin resistance gene MCR-2 of *E. coli* with the antibacterial phage loaded Cas13a.

In this example, M13 phage was loaded with crRNA and Cas13a for the target sequence in which strong bactericidal activity was confirmed in the above Example 1. *E. coli* of the NEB 5-alpha F'l$^{q}$ strain was transformed with an expression plasmid of the carbapenem resistance gene bla$_{IMP\text{-}1}$ and the colistin resistance gene MCR-2. The prepared *E. coli* was infected with the antibacterial phage prepared in the same manner as in Example 1 and cultured for 6 hours. They were cultured on LB soft agar medium without antibiotics to create a dilution series of liquids. Each sample was plated on an LB plate, an ampicillin-containing LB plate, and a colistin-containing LB plate. After culturing all the plates at 37 degree C. for 12 hours, the number of colonies growing on the plates was counted. Bacteria grown on the ampicillin-containing LB plate were used as the bla$_{IMP\text{-}1}$ expressing strain, bacteria growing on the colistin-containing LB plate were used as the MCR-2 expressing strain, and other bacteria were used as the control strains, and the ratio of each strain was calculated.

The antibacterial phage targeting bla$_{IMP\text{-}1}$ reduced the number of bla$_{IMP\text{-}1}$ expression strains, and the antibacterial phage targeting MCR-2 reduced the number of MCR-2 expression strains, respectively. That is, the Cas13a-loaded antibacterial phage could be used to reduce *E. coli* carrying a specific gene.

(Optimization of CRISPR-Cas13a Expression Vector Targeting the Bla$_{IMP\text{-}1}$ Gene)

Figure 12:
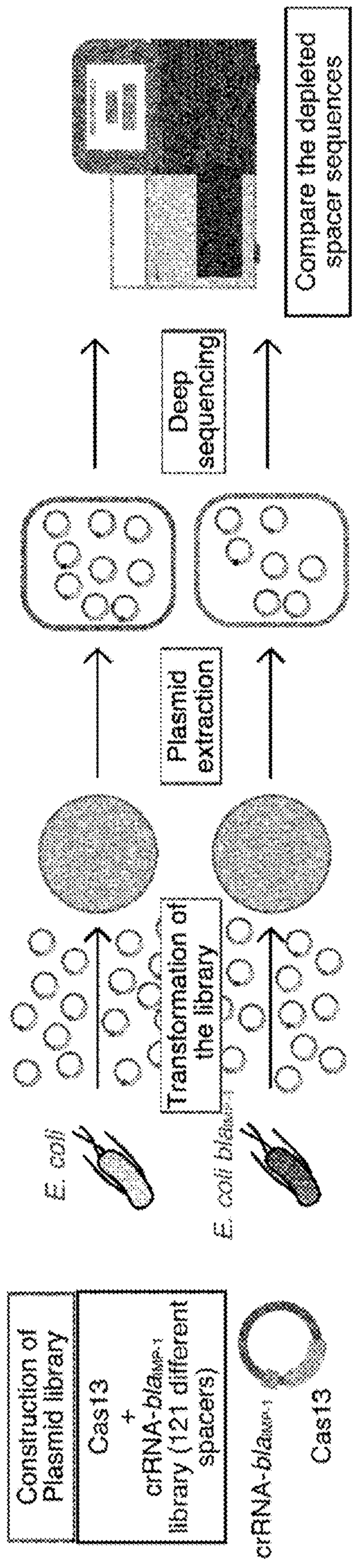
FIG. 12 is a conceptual diagram of a method for investigating the optimum CRISPR sequence in the bactericidal effect of antibacterial phage according to Example 2 of the present invention.

FIG. 12 is a conceptual diagram of a method for investigating the optimum CRISPR sequence for the bactericidal effect of a bacterium having the bla$_{IMP\text{-}1}$ gene by CRISPR-Cas13a.

We have prepared 121 kinds of different spacers targeting bla$_{IMP\text{-}1}$ were inserted into pKLC21.

Table 4 below shows the relationship between the SEQ ID NO: (No.) of the sequence listing, the name of the sequence for the bla$_{IMP\text{-}1}$ gene (Spacer name), and the selected target site base sequence (Target Sequence, Spacer Sequence).

TABLE 4

| No. | Spacer name | Spacer sequence |
|---|---|---|
| 1 | IMP-1_11 | CAAAACAAAAATATAAAGAATACAGATA |
| 2 | IMP-1_14 | CTGCAAAACAAAAATATAAAGAATACAG |
| 3 | IMP-1_19 | CAATGCTGCAAAACAAAAATATAAAGAA |
| 4 | IMP-1_22 | TAGCAATGCTGCAAAACAAAAATATAAA |
| 5 | IMP-1_23 | GTAGCAATGCTGCAAAACAAAAATATAA |
| 6 | IMP-1_25 | CGGTAGCAATGCTGCAAAACAAAAATAT |
| 7 | IMP-1_28 | CTGCGGTAGCAATGCTGCAAAACAAAAA |
| 8 | IMP-1_34 | ACTCTGCTGCGGTAGCAATGCTGCAAAA |
| 9 | IMP-1_39 | CAAAGACTCTGCTGCGGTAGCAATGCTG |
| 10 | IMP-1_40 | GCAAAGACTCTGCTGCGGTAGCAATGCT |
| 11 | IMP-1_60 | CTTTTCAATTTTTAAATCTGGCAAAGAC |
| 12 | IMP-1_71 | CCTTCATCAAGCTTTTCAATTTTTAAAT |
| 13 | IMP-1_81 | AACATAAACGCCTTCATCAAGCTTTTCA |
| 14 | IMP-1_85 | TATGAACATAAACGCCTTCATCAAGCTT |
| 15 | IMP-1_88 | AAGTATGAACATAAACGCCTTCATCAAG |
| 16 | IMP-1_104 | TTAACTTCTTCAAACGAAGTATGAACAT |
| 17 | IMP-1_113 | CCCCACCCGTTAACTTCTTCAAACGAAG |
| 18 | IMP-1_120 | AACAACGCCCCACCCGTTAACTTCTTCA |
| 19 | IMP-1_121 | GAACAACGCCCCACCCGTTAACTTCTTC |
| 20 | IMP-1_126 | TTTAGGAACAACGCCCCACCCGTTAACT |
| 21 | IMP-1_141 | AACCACCAAACCATGTTTAGGAACAACG |
| 22 | IMP-1_151 | CATTTACAAGAACCACCAAACCATGTTT |
| 23 | IMP-1_157 | CCTCAGCATTTACAAGAACCACCAAACC |
| 24 | IMP-1_161 | TAAGCCTCAGCATTTACAAGAACCACCA |
| 25 | IMP-1_162 | GTAAGCCTCAGCATTTACAAGAACCACC |
| 26 | IMP-1_170 | TCAATTAGGTAAGCCTCAGCATTTACAA |
| 27 | IMP-1_172 | TGTCAATTAGGTAAGCCTCAGCATTTAC |
| 28 | IMP-1_174 | AGTGTCAATTAGGTAAGCCTCAGCATTT |
| 29 | IMP-1_175 | GAGTGTCAATTAGGTAAGCCTCAGCATT |
| 30 | IMP-1_181 | TAAATGGAGTGTCAATTAGGTAAGCCTC |
| 31 | IMP-1_184 | CCGTAAATGGAGTGTCAATTAGGTAAGC |
| 32 | IMP-1_193 | TATCTTTAGCCGTAAATGGAGTGTCAAT |
| 33 | IMP-1_206 | ACTAACTTTTCAGTATCTTTAGCCGTAA |
| 34 | IMP-1_208 | TGACTAACTTTTCAGTATCTTTAGCCGT |
| 35 | IMP-1_222 | CTCCACAAACCAAGTGACTAACTTTTCA |
| 36 | IMP-1_227 | CCACGCTCCACAAACCAAGTGACTAACT |
| 37 | IMP-1_242 | CCTTTTATTTTATAGCCACGCTCCACAA |
| 38 | IMP-1_245 | CTGCCTTTTATTTTATAGCCACGCTCCA |
| 39 | IMP-1_250 | AAATGCTGCCTTTTATTTTATAGCCACG |

TABLE 4-continued

| No. | Spacer name | Spacer sequence |
|---|---|---|
| 40 | IMP-1_251 | GAAATGCTGCCTTTTATTTTATAGCCAC |
| 41 | IMP-1_253 | AGGAAATGCTGCCTTTTATTTTATAGCC |
| 42 | IMP-1_255 | AGAGGAAATGCTGCCTTTTATTTTATAG |
| 43 | IMP-1_261 | AAAATGAGAGGAAATGCTGCCTTTTATT |
| 44 | IMP-1_266 | CTATGAAAATGAGAGGAAATGCTGCCTT |
| 45 | IMP-1_269 | TCGCTATGAAAATGAGAGGAAATGCTGC |
| 46 | IMP-1_272 | CTGTCGCTATGAAAATGAGAGGAAATGC |
| 47 | IMP-1_274 | TGCTGTCGCTATGAAAATGAGAGGAAAT |
| 48 | IMP-1_278 | CCCGTGCTGTCGCTATGAAAATGAGAGG |
| 49 | IMP-1_291 | CCACTCTATTCCGCCCGTGCTGTCGCTA |
| 50 | IMP-1_298 | AATTAAGCCACTCTATTCCGCCCGTGCT |
| 51 | IMP-1_300 | AGAATTAAGCCACTCTATTCCGCCCGTG |
| 52 | IMP-1_304 | ATCGAGAATTAAGCCACTCTATTCCGCC |
| 53 | IMP-1_308 | ATAGATCGAGAATTAAGCCACTCTATTC |
| 54 | IMP-1_309 | GATAGATCGAGAATTAAGCCACTCTATT |
| 55 | IMP-1_310 | GGATAGATCGAGAATTAAGCCACTCTAT |
| 56 | IMP-1_311 | GGGATAGATCGAGAATTAAGCCACTCTA |
| 57 | IMP-1_322 | ATGCATACGTGGGGATAGATCGAGAATT |
| 58 | IMP-1_331 | TTAATTCAGATGCATACGTGGGGATAGA |
| 59 | IMP-1_339 | TTCATTTGTTAATTCAGATGCATACGTG |
| 60 | IMP-1_342 | CAGTTCATTTGTTAATTCAGATGCATAC |
| 61 | IMP-1_353 | TCTTTTTTAAGCAGTTCATTTGTTAATT |
| 62 | IMP-1_363 | AACCTTACCGTCTTTTTTAAGCAGTTCA |
| 63 | IMP-1_367 | CTTGAACCTTACCGTCTTTTTTAAGCAG |
| 64 | IMP-1_368 | GCTTGAACCTTACCGTCTTTTTTAAGCA |
| 65 | IMP-1_370 | TGGCTTGAACCTTACCGTCTTTTTTAAG |
| 66 | IMP-1_376 | AATTTGTGGCTTGAACCTTACCGTCTTT |
| 67 | IMP-1_383 | CTAAATGAATTTGTGGCTTGAACCTTAC |
| 68 | IMP-1_392 | TTAACTCCGCTAAATGAATTTGTGGCTT |
| 69 | IMP-1_399 | CCAATAGTTAACTCCGCTAAATGAATTT |
| 70 | IMP-1_429 | ATAAAAAACTTCAATTTTATTTTTAACT |
| 71 | IMP-1_430 | GATAAAAAACTTCAATTTTATTTTTAAC |
| 72 | IMP-1_434 | CCTGGATAAAAAACTTCAATTTTATTTT |
| 73 | IMP-1_435 | GCCTGGATAAAAAACTTCAATTTTATTT |
| 74 | IMP-1_436 | GGCCTGGATAAAAAACTTCAATTTTATT |
| 75 | IMP-1_441 | TCCCGGGCCTGGATAAAAAACTTCAATT |
| 76 | IMP-1_443 | TGTCCCGGGCCTGGATAAAAAACTTCAA |
| 77 | IMP-1_445 | TGTGTCCCGGGCCTGGATAAAAAACTTC |
| 78 | IMP-1_447 | AGTGTGTCCCGGGCCTGGATAAAAAACT |

TABLE 4-continued

| No. | Spacer name | Spacer sequence |
|---|---|---|
| 79 | IMP-1_448 | GAGTGTGTCCCGGGCCTGGATAAAAAAC |
| 80 | IMP-1_455 | TTATCTGGAGTGTGTCCCGGGCCTGGAT |
| 81 | IMP-1_471 | CAACCAAACCACTACGTTATCTGGAGTG |
| 82 | IMP-1_472 | GCAACCAAACCACTACGTTATCTGGAGT |
| 83 | IMP-1_491 | AATAATATTTTCCTTTCAGGCAACCAAA |
| 84 | IMP-1_510 | TTTAATAAAACAACCACCGAATAATATT |
| 85 | IMP-1_511 | GTTTAATAAAACAACCACCGAATAATAT |
| 86 | IMP-1_515 | TACGGTTTAATAAAACAACCACCGAATA |
| 87 | IMP-1_524 | CCTAAACCGTACGGTTTAATAAAACAAC |
| 88 | IMP-1_536 | TCACCCAAATTGCCTAAACCGTACGGTT |
| 89 | IMP-1_538 | CGTCACCCAAATTGCCTAAACCGTACGG |
| 90 | IMP-1_550 | CTTCTATATTTGCGTCACCCAAATTGCC |
| 91 | IMP-1_555 | CCAAGCTTCTATATTTGCGTCACCCAAA |
| 92 | IMP-1_556 | GCCAAGCTTCTATATTTGCGTCACCCAA |
| 93 | IMP-1_562 | ACTTTGGCCAAGCTTCTATATTTGCGTC |
| 94 | IMP-1_563 | GACTTTGGCCAAGCTTCTATATTTGCGT |
| 95 | IMP-1_565 | CGGACTTTGGCCAAGCTTCTATATTTGC |
| 96 | IMP-1_566 | GCGGACTTTGGCCAAGCTTCTATATTTG |
| 97 | IMP-1_580 | ACTTTAATAATTTGGCGGACTTTGGCCA |
| 98 | IMP-1_581 | GACTTTAATAATTTGGCGGACTTTGGCC |
| 99 | IMP-1_595 | CCTTACCATATTTGGACTTTAATAATTT |
| 100 | IMP-1_600 | TTTTGCCTTACCATATTTGGACTTTAAT |
| 101 | IMP-1_609 | AACAACCAGTTTTGCCTTACCATATTTG |
| 102 | IMP-1_610 | GAACAACCAGTTTTGCCTTACCATATTT |
| 103 | IMP-1_615 | ACTTGGAACAACCAGTTTTGCCTTACCA |
| 104 | IMP-1_617 | TGACTTGGAACAACCAGTTTTGCCTTAC |
| 105 | IMP-1_632 | TCTCCAACTTCACTGTGACTTGGAACAA |
| 106 | IMP-1_634 | CGTCTCCAACTTCACTGTGACTTGGAAC |
| 107 | IMP-1_637 | ATGCGTCTCCAACTTCACTGTGACTTGG |
| 108 | IMP-1_639 | TGATGCGTCTCCAACTTCACTGTGACTT |
| 109 | IMP-1_641 | AGTGATGCGTCTCCAACTTCACTGTGAC |
| 110 | IMP-1_648 | TTTCAAGAGTGATGCGTCTCCAACTTCA |
| 111 | IMP-1_652 | TAAGTTTCAAGAGTGATGCGTCTCCAAC |
| 112 | IMP-1_660 | CTCTAATGTAAGTTTCAAGAGTGATGCG |
| 113 | IMP-1_664 | CCTGCTCTAATGTAAGTTTCAAGAGTGA |
| 114 | IMP-1_680 | TTTAACCCTTTAACCGCCTGCTCTAATG |
| 115 | IMP-1_693 | TTTTTTACTTTCGTTTAACCCTTTAACC |
| 116 | IMP-1_694 | GTTTTTTACTTTCGTTTAACCCTTTAAC |
| 117 | IMP-1_697 | ATGGTTTTTTACTTTCGTTTAACCCTTT |
| 118 | IMP-1_702 | TTTTGATGGTTTTTTACTTTCGTTTAAC |
| 119 | IMP-1_703 | GTTTTGATGGTTTTTTACTTTCGTTTAA |
| 120 | IMP-1_707 | CTTGGTTTTGATGGTTTTTTACTTTCGT |
| 121 | IMP-1_710 | TTGCTTGGTTTTGATGGTTTTTTACTTT |

The above-mentioned 121 kinds of plasmid vectors were mixed in equal amounts to prepare a plasmid library. This plasmid library used to transform *E. coli* MC1061 pKLC26 or bMC1061 pKLC26 $bla_{IMP\text{-}1}$, and each of them was plated on twenty LB plates (containing chloramphenicol and kanamycin). After culturing at 37 degree C. for 16 hours, it was confirmed that the number of colonies was 10,000 or more in each plate group, 5 ml of medium was added to the plates, and all colonies were collected with a scraper. After centrifuging the bacterium, the plasmid was extracted by using QIAGEN Plasmid Midi Kit (manufactured by QIAGEN), and the nucleotide sequence was sequenced by Illumina MiSeq. A plasmid library of mate-pair was prepared by using the Nextera mate-pair sample preparation kit (manufactured by Illumina, Inc., San Diego, CA, USA), and the plasmid library was sequenced by MiSeq reagent kit version 3 (Illumina, Inc.). After that, the number of each spacer sequence was counted.

Figure 13:
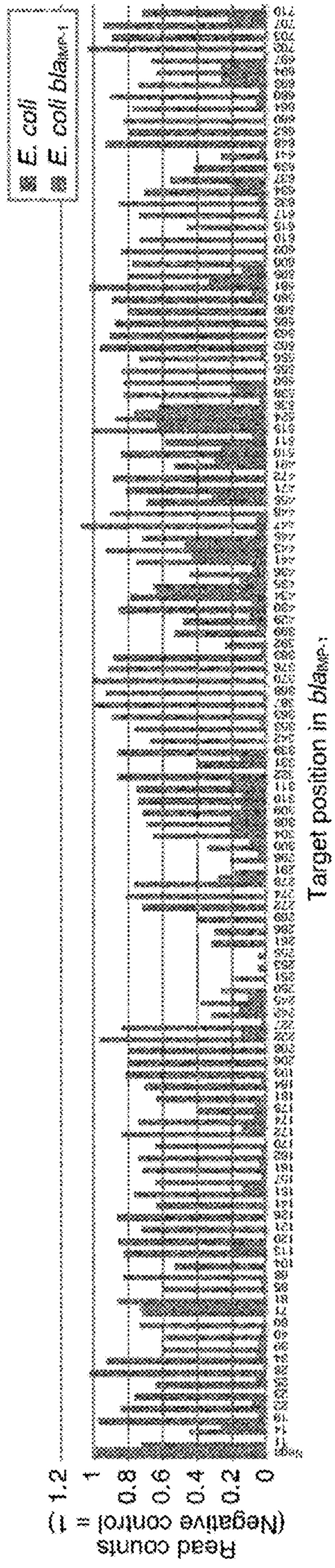
FIG. 13 is a graph showing a bactericidal effect of antibacterial phage according to Example 2 of the present invention.

FIG. 13 is a diagram showing the bactericidal effect of CRISPR-Cas13a on which 121 types of $bla_{IMP\text{-}1}$ spacer sequences are separately loaded on *E. coli* MC1061 having the $bla_{IMP\text{-}1}$ gene. When the spacer sequences are No. 563 (GACTTTGGCCAAGCTTCTATATTTGCGT), No. 566 (GCGGACTTTGGCCAAGCTTCTATATTTG), No. 702 (TTTTGATGGTTTTTTACTTTCGTTTAAC), No. 562 (ACTTTGGCCAAGCTTCTATATTTGCGTC), No. 370 (TGGCTTGAACCTTACCGTCTTTTTTAAG), No. 565 (CGGACTTTGGCCAAGCTTCTATATTTGC), No. 193 (TATCTTTAGCCGTAAATGGAGTGTCAAT), No. 274 (TGCTGTCGCTATGAAAATGAGAGGAAAT), No. 648 (TTTCAAGAGTGATGCGTCTCCAACTTCA), No. 11 (CAAAACAAAAATATAAAGAATACAGATA), No. 609 (AACAACCAGTTTTGCCTTACCATATTTG), No. 703 (GTTTTGATGGTTTTTTACTTTCGTTTAA), and No. 208 (TGACTAACTTTTCAGTATCTTTAGCCGT), the sequence count of the $bla_{IMP\text{-}1}$ having strain was 100 times or more lower than that of the $bla_{IMP\text{-}1}$ non-having strain. In the following experiment, the spacer sequence targeting $bla_{IMP\text{-}1}$ is used No. 563, which has the highest inhibitory effect.

(Method of Increasing Gene Detection Sensitivity of Antibacterial Phage)

Next, in order to increase the gene detection sensitivity of the antibacterial phage, the present inventors conducted an experiment in which the antibacterial phage included an antibiotic resistance gene to detect the gene.

Figure 14A:
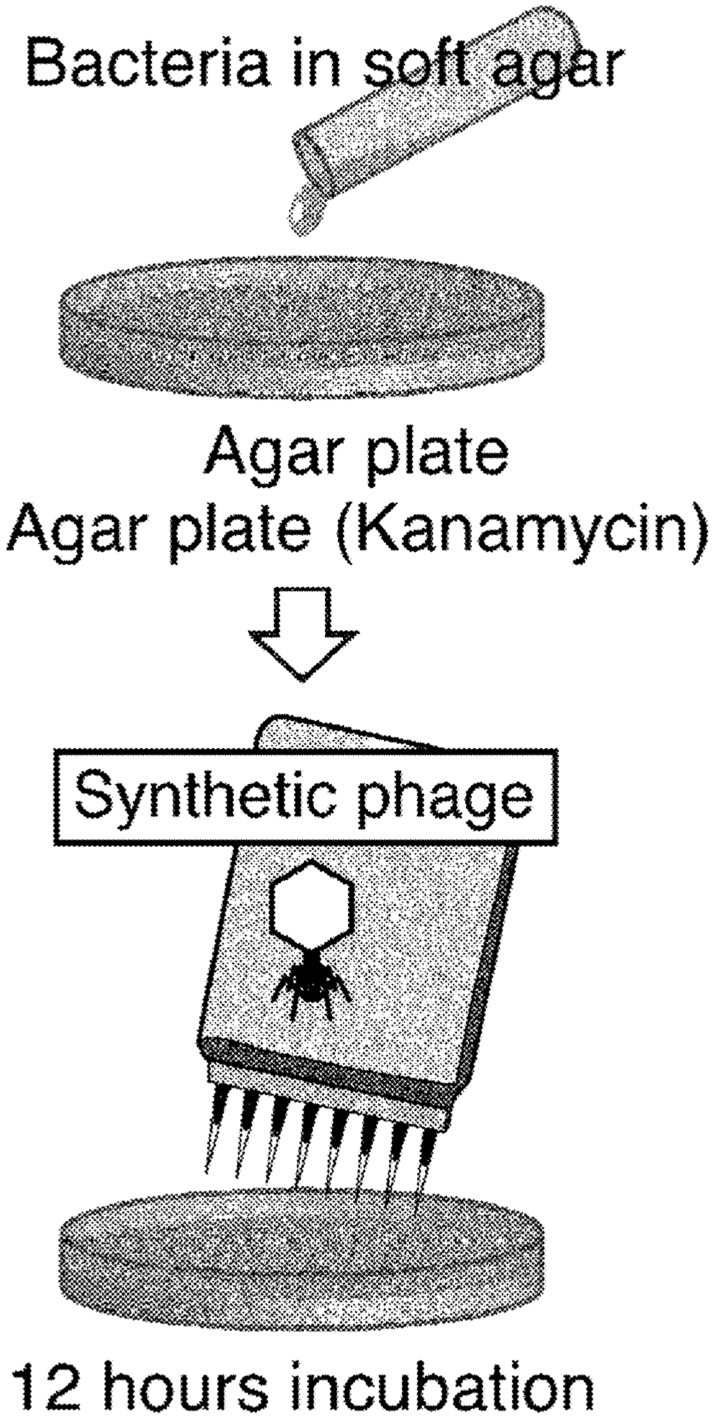
FIG. 14 is a diagram and a photograph showing the result of increasing the sensitivity of detection of a specific gene according to Example 2 of the present invention.

FIG. 14A shows a conceptual diagram how to increase the sensitivity of gene detection of antibacterial phage. M13-based antibacterial phage carrying the CRISPR-Cas13a sequence and the kanamycin resistance gene sequence was synthesized. A detection experiment was carried out by using an agar plate containing no kanamycin (Agar plate) and an agar plate containing kanamycin (Agar plate (Kanamycin)). The product of a mixture of the target bacterium (NEB5-alpha $F'I^q$ pKLC26 $bla_{IMP\text{-}1}$) and soft agar medium was poured and left to be hardened. Immediately y after the plate had hardened, antibacterial phage was added from above, and the bacteria were cultured at 37 degree C. for 12 hours.

Figure 14B:
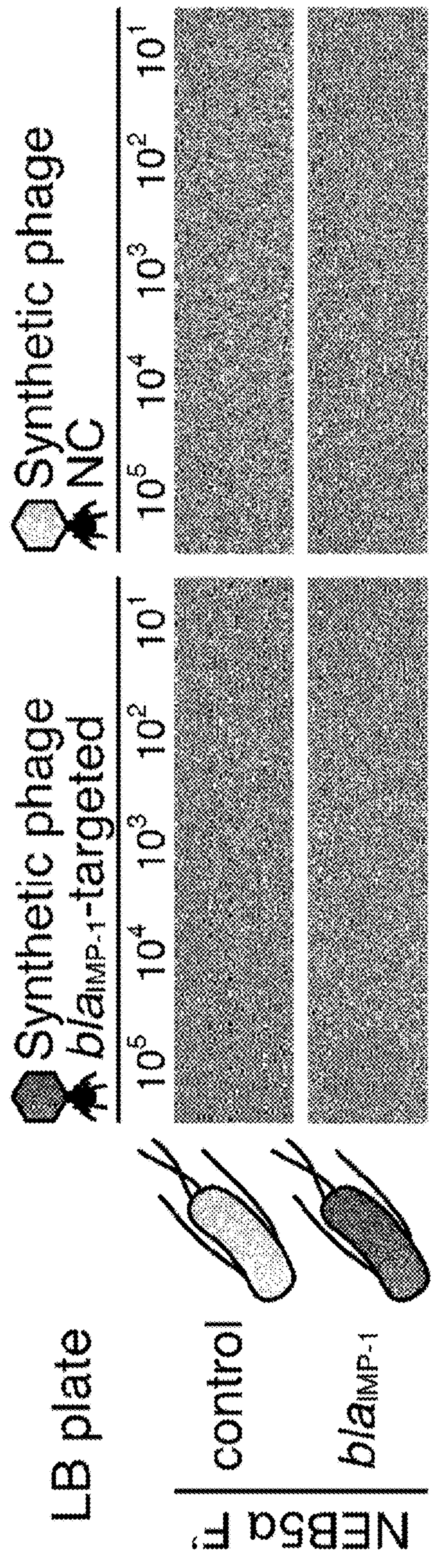
Figure 14C:
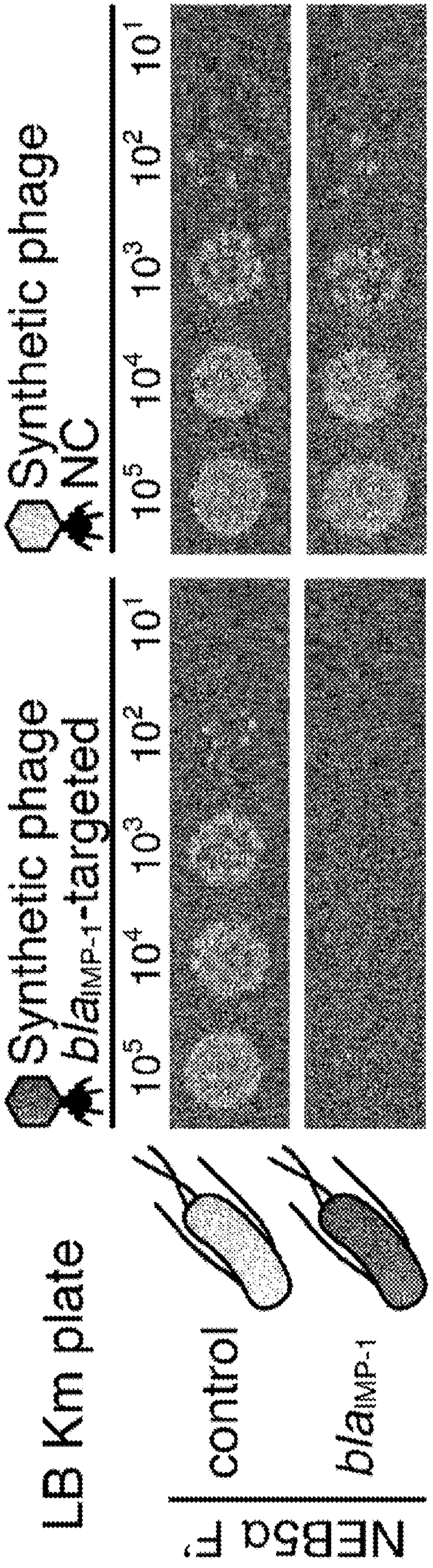

FIG. 14B shows the experimental results on the kanamycin-free agar plate, and FIG. 14C shows the experimental results on the kanamycin-containing agar plate. Regarding the control (strain not carrying $bla_{IMP-1}$) and the strain carrying $bla_{IMP-1}$, respectively, photographs of the results for each TFU are shown for those with the target gene introduced ($bla_{IMP-1}$-targeted) and those without the target gene (NC).

In this experiment, when cultured in an agar plate containing no antibiotic (agar plate containing no antibiotic) for the resistance gene possessed by the phage as in Example 1, for detection, it was necessary to use antibacterial phage in the range of $10^4$ TFU to $10^5$ TFU.

On the other hand, it was confirmed that when the antibacterial phage had an antibiotic resistance gene, it can be sufficiently detected even at about $10^3$ TFU. That is, the detection sensitivity of the gene could be increased about 100 times. Since this method only causes the antibacterial phage to carry the resistance gene, it can be applied not only to M13 phage but also to all other antibacterial phage.

(Identification of Carbapenem Resistance Gene by Antibacterial Phage)

Figure 15:
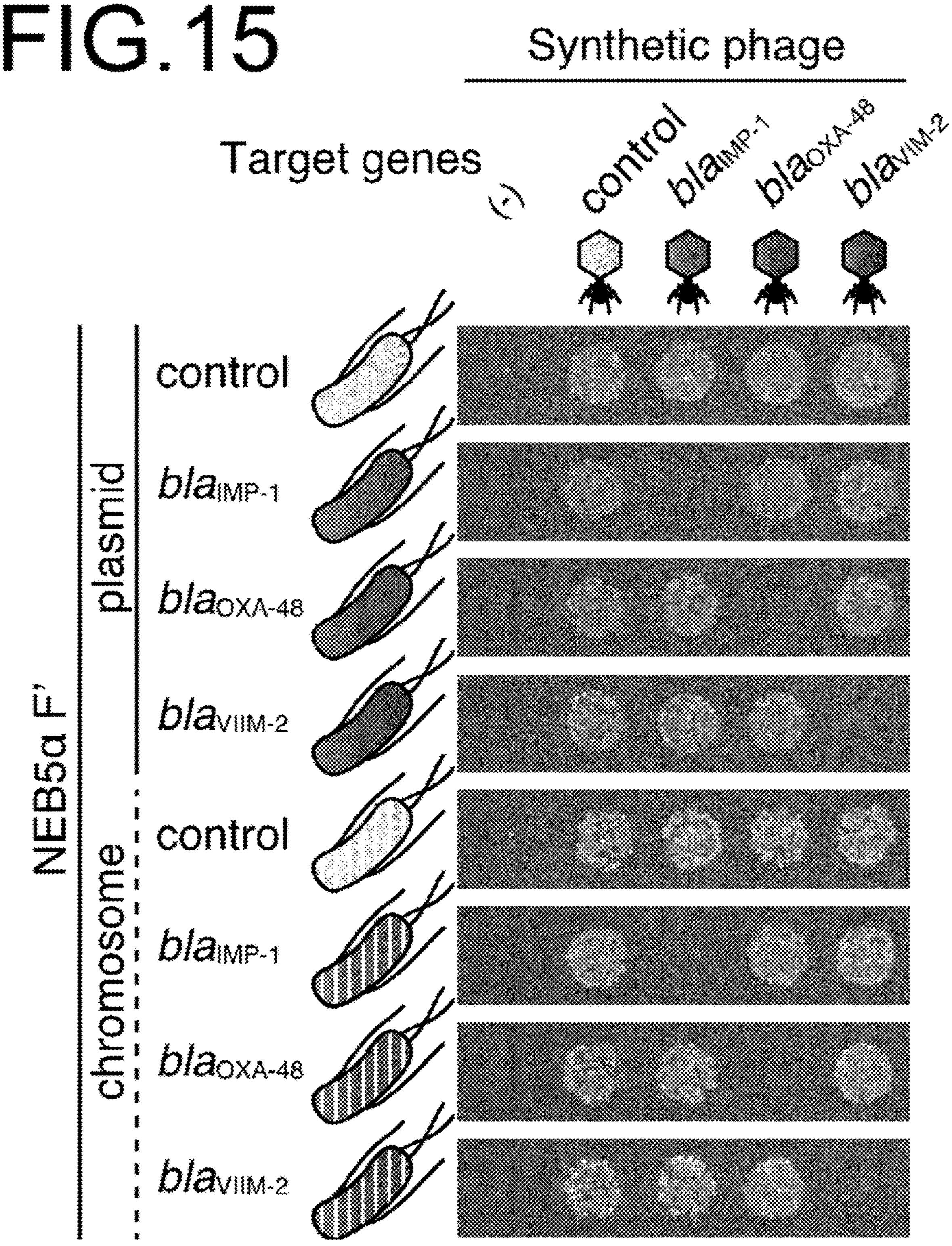
FIG. 15 is a photograph showing the results of identifying carbapenem resistance genes by using the method shown in FIG. 14.

FIG. 15 is a photograph in which the carbapenem resistance genes $bla_{IMP-1}$, $bla_{OXA-48}$, and $bla_{VIM-2}$ were identified by using the method of FIG. 14. The *E. coli* NEB5-alpha $F'I^q$ expressing a resistance gene from the pKLC26 plasmid (plasmid) or NEB5-alpha $F'I^q$ expressing the resistance gene from the genome (chromosome) were prepared, $10^4$ TFU antibacterial phage were added in the same manner as in FIG. 14, and the result of culturing at 37 degree C. for 12 hours were shown.

For each, the results for the control having no carbapenem resistance gene, for $bla_{IMP-1}$, $bla_{OXA-48}$, and $bla_{VIM-2}$, for which the target gene was added, and for the negative control (−) of adding only water were shown. As a result, the bacteria having each gene are selectively lysed can be seen.

The method for expressing the resistance gene on the chromosome of the *E. coli* NEB5-alpha $F'I^q$ strain was as follows. NEB5-alpha $F'I^q$ was transformed by PKD46 into and selectively cultured on an ampicillin-containing LB plate. Also, the drug resistance gene encoded by pKLC26 vector was amplified by the primers, K12 genome-in pKLC26-f, "CCCTTCAACCTTAGCAGTAGCGTGGGATGATTTCACAATTAGAAAGACCTTGACGCAC ACCGTGGAAAC" and K12 genome-in pKLC26Cm-r, "TGTCCTGCACGACGCCTTGCGTCACTAGCCTCTTCTCTAGCTCATCATGCTGAGACGT TGATCGGCACG". The amplified DNA was designed to include the target drug resistance gene and the chloramphenicol resistance gene, and the insertion site was designed in a non-coding region that is not conserved between species. The NEB5-alpha $F'I^q$ pKD46 strain or MC1061 pKD46 strain was cultured in an ampicillin-containing LB medium, and when the OD600 reached 0.2, L-arabinose was added to a final concentration of 0.3%, and the bacteria were vigorously shake-cultured for 15 minutes at 42 degree C. After washing 3 times with ice-cold 10% glycerol, 100 ng of amplified DNA fragments (having homologous sequences to *E. coli* at the 5'- and 3'-ends) are transferred to an ice-cooled 1 mm cuvette and electroporated with ELEPO21 (Poring Pulse (Voltage: 2,000 V, Pulse width: 2.5 msec, Pulse interval: 50 ms, Number of times: 1, Polarity: +), Transfer Pulse (Voltage: 150 V, Pulse width: 50 msec, Pulse interval: 50 ms, Number of times: 5, Polarity: +/−)) was performed. Immediately, 1 mL SOC was added, and the mixture was shake-cultured at 37 degree C., and then, it was selectively cultured on an LB plate containing chloramphenicol. The sequence around the modification of the genetically modified *E. coli*, which was produced here, was confirmed by sequencing of the Sanger method.

(Identification of Toxin Genes by Antibacterial Phage)

Figure 16:
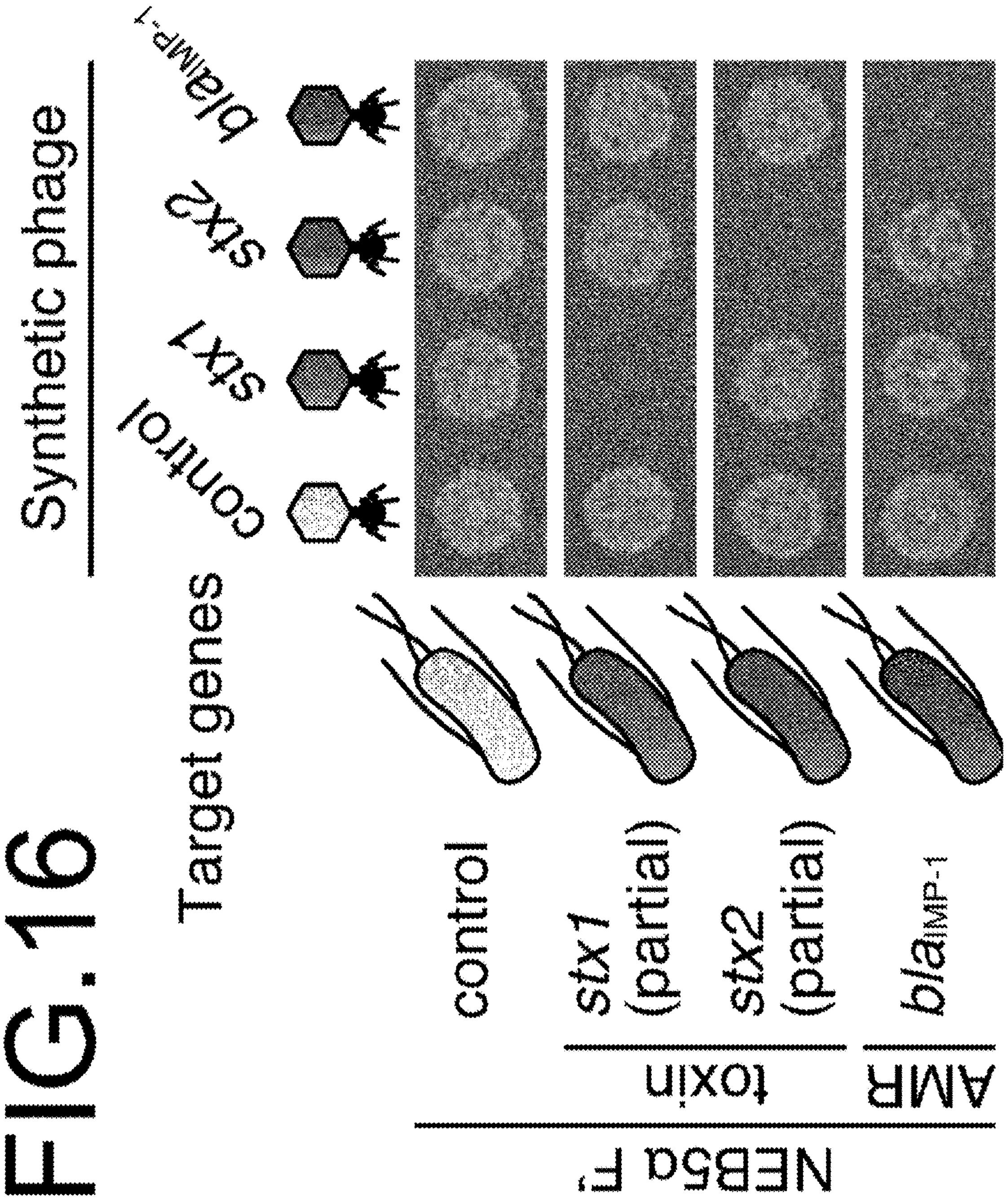
FIG. 16 is a photograph showing the results of identification between the Shiga toxin-producing gene and the carbapenem resistance gene according to Example 2 of the present invention.

FIG. 16 is a photograph in which the toxin genes stx1 and stx2 were identified by using antibacterial phage. Specifically, the control and each toxin gene (toxin) stx1 and stx2, and resistance gene (AMR) could be detected by antibacterial phage.

Note that stx1 and stx2 use a part of the arrangement, not the total length. It is amplified from the pKLC26 plasmid with primers, pKLC26 stx1 partial PCR SacI-r, "GTGGAGCTCGGTCATGGCATTTCCACTAAACTCCATTAAGAGAATGGATT TTGTGATGC", pKLC26 stx1 partial PCR SacI-f, "ACCGAGCTCCACCGGAAGAAGTGGAACTCACACTGAACGAATTCGATCCTCTAGAGTC", pKLC26 stx2 partial PCR SacI-r, "GCGGAGCTCGGTCATTGTATTACCACTGAACTCCATTAAGAGAATGGATTTTGTGATG C", and pKLC26 stx2 partial PCR SacI-f, "ACCGAGCTCCGCCGGGAGACGTGGACCTCACTCTGAACGAATTCGATCCTCTAGAGTC", and after processing with SacI (manufactured by TakaRa Bio), it is ligated by using "Ligation High Ver. 2" (manufactured by TOYOBO). (Hereinafter, each is referred to as "pKLC26 stx1 vector" and "pKLC26 stx2 vector").

In addition, a double-stranded DNA annealed with stx1 488-as, "TATCCTAATGGAGTTTAGTGGAAATGCCATGAC" and stx1 488-s, "AAACGTCATGGCATTTCCACTAAACTCCATTAG" or a double-stranded DNA annealed with stx2 488-as, "TATCCTAATGGAGTTCAGTGGTAATACAATGAC" and stx2 488-s, "AAACGTCATTGTATTACCACTGAACTCCATTAG" was inserted into the BsaI site of pKLC21, and "pKLC21 BsaI stx1_488 vector" and "pKLC21 BsaI stx2_488 vector" were produced. By using these, the toxin genes stx1 and stx2 were detected by the same method as shown in FIG. 14.

(Differentiation of Carbapenem Resistance Gene by Antibacterial Phage in Clinical Isolate)

Figure 17:
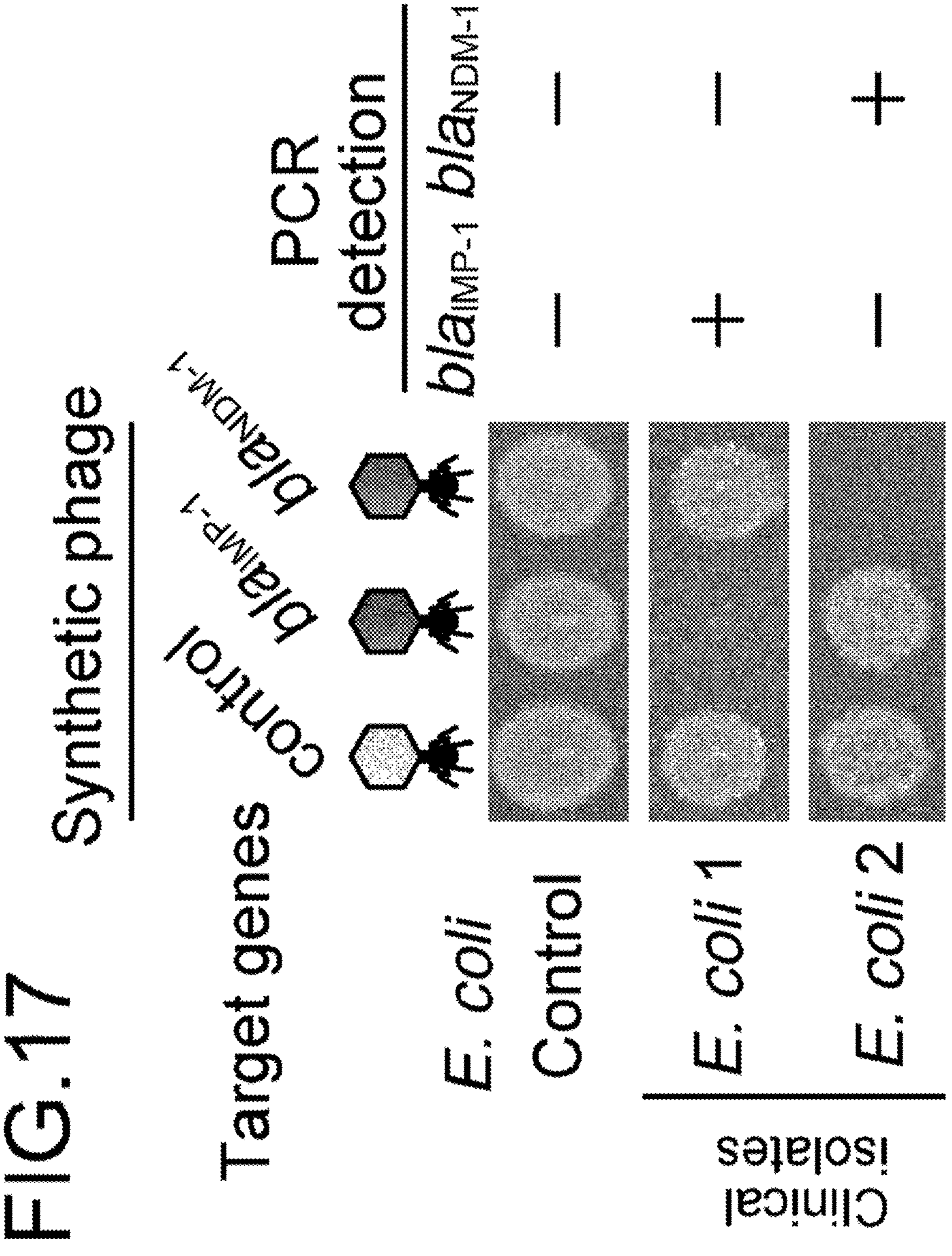
FIG. 17 is a diagram and a photograph showing the results of identification of carbapenem resistance genes of the clinically isolated *E. coli* strain according to Example 2 of the present invention.

FIG. 17 is a photograph in which the carbapenem resistance genes $bla_{IMP-1}$ and $bla_{NDM-1}$ were identified to clinical isolates (*E. coli*1 and *E. coli*2) infected with antibacterial phage. These clinical isolates were obtained and maintained from an unspecified patient at Jichi Medical University.

The expression of $bla_{IMP-1}$ and $bla_{NDM-1}$ of the clinical isolates (*E. coli*1 and *E. coli*2) was confirmed by PCR reaction by using primers, IMP type det 255-f, "GGCGTTTATGTTCATACTTCG" and IMP type det 255-r, "AGATGCATACGTGGGGATAG", and NDM type det 209-f, "CCAATGCGTTGTCGAACCAG" and NDM type det 209-r, "GATCAGGCAGCCACCAAAAG".

(Therapeutic Effect of Antibacterial Phage on Moth Larvae Infected with Clinically Isolated *E. coli* Strain)

Figure 18:
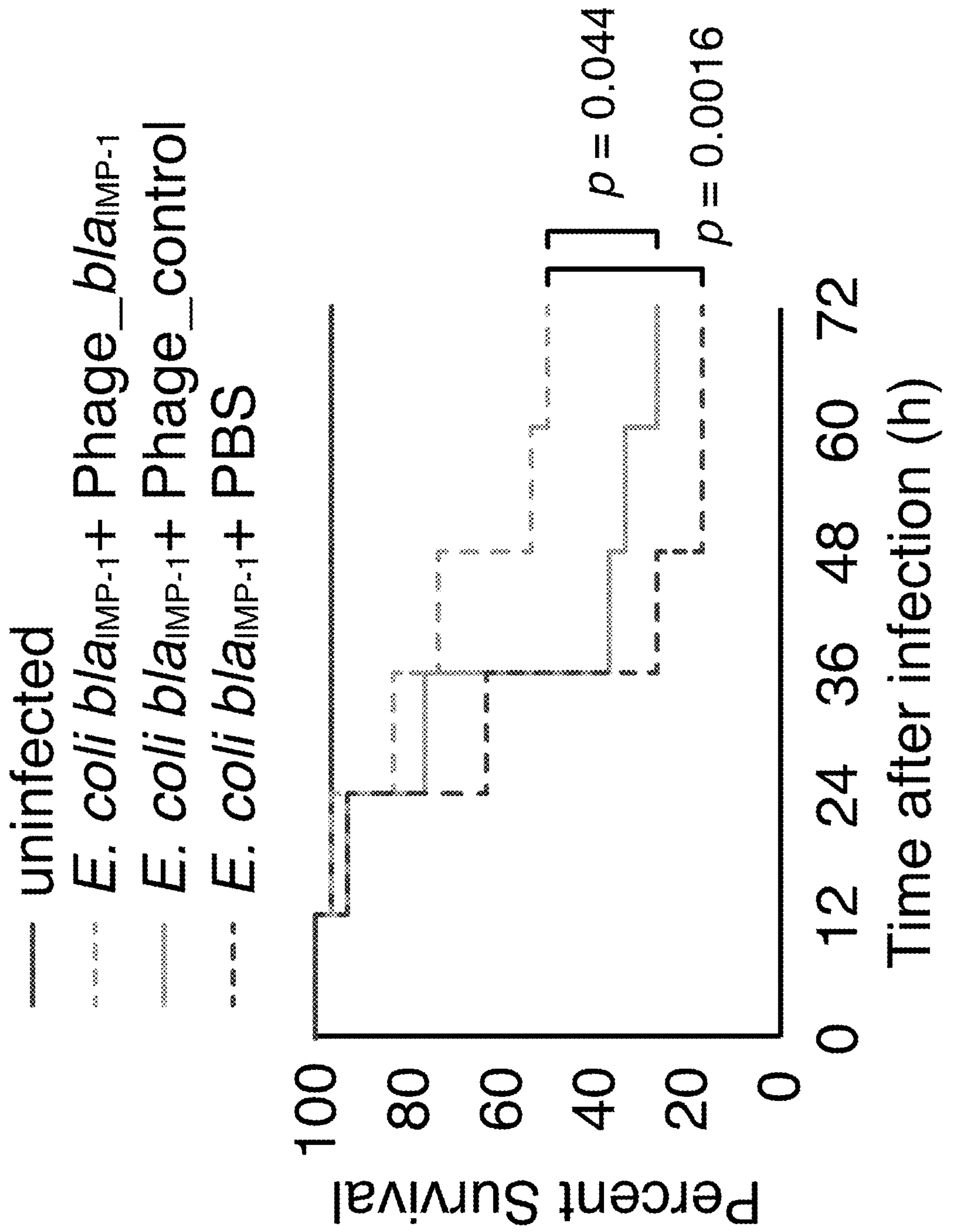
FIG. 18 is a graph showing the therapeutic effect of antibacterial phage on moth larvae infected with the clinically isolated *Escherichia coli* strain according to Example 2 of the present invention.

FIG. 18 is a graph examining the therapeutic effect of antibacterial phage on moth larvae infected with a clinically isolated *E. coli* strain.

M-sized larvae of *Galleria mellonella* were purchased from the "Live Bait Factory, inc." and used for the survival assay. After obtaining, they were acclimatized to the laboratory environment in the dark for 24 hours and then used for assay within 48 hours. In addition, larvae that were weak in movement, dark in color, unusual in shape, and clearly different in size from other larvae were not used in the experiment. The syringe used was a combination of a Hamilton syringe, leur tip (701LT, Hamilton) and a KF731 needle (Hamilton). *E. coli* cultured at 37 degree C. in LB medium overnight was added to LB medium in an amount of 1/100 and shake-cultured at 37 degree C. until OD600 reached about 0.5. It was then washed twice with PBS to make a solution of ~$1\times10^7$ CFU/ml. Twenty cream-colored larvae were taken, and 5 micro-l of PBS or bacterial solution was injected into the left proleg. One hour later, 5 micro-l each of SM buffer or antibacterial phage was injected into the right proleg. After that, the larvae were moved to an incubator at 37 degree C., and the progress was observed every 12 hours. Larvae that stopped responding to touch were determined to be dead.

According to the graph of FIG. 18, 80% of the larvae to which the clinically isolated *E. coli* expressing $bla_{IMP\text{-}1}$ Was administered died after 48 hours. On the other hand, the mortality rate in the group to which the antibacterial phage targeting $bla_{IMP\text{-}1}$ was administered was about 50%, and there was a statistically significant difference in the mortality rate between the two groups. From this result, it was confirmed that the prepared antibacterial phage targeting blamMP-1 has a therapeutic effect on bacterial infections in an experimental system in vivo.

(Identification of *Staphylococcus aureus* Methicillin Resistance Gene by Antibacterial Phage)

Figure 19:
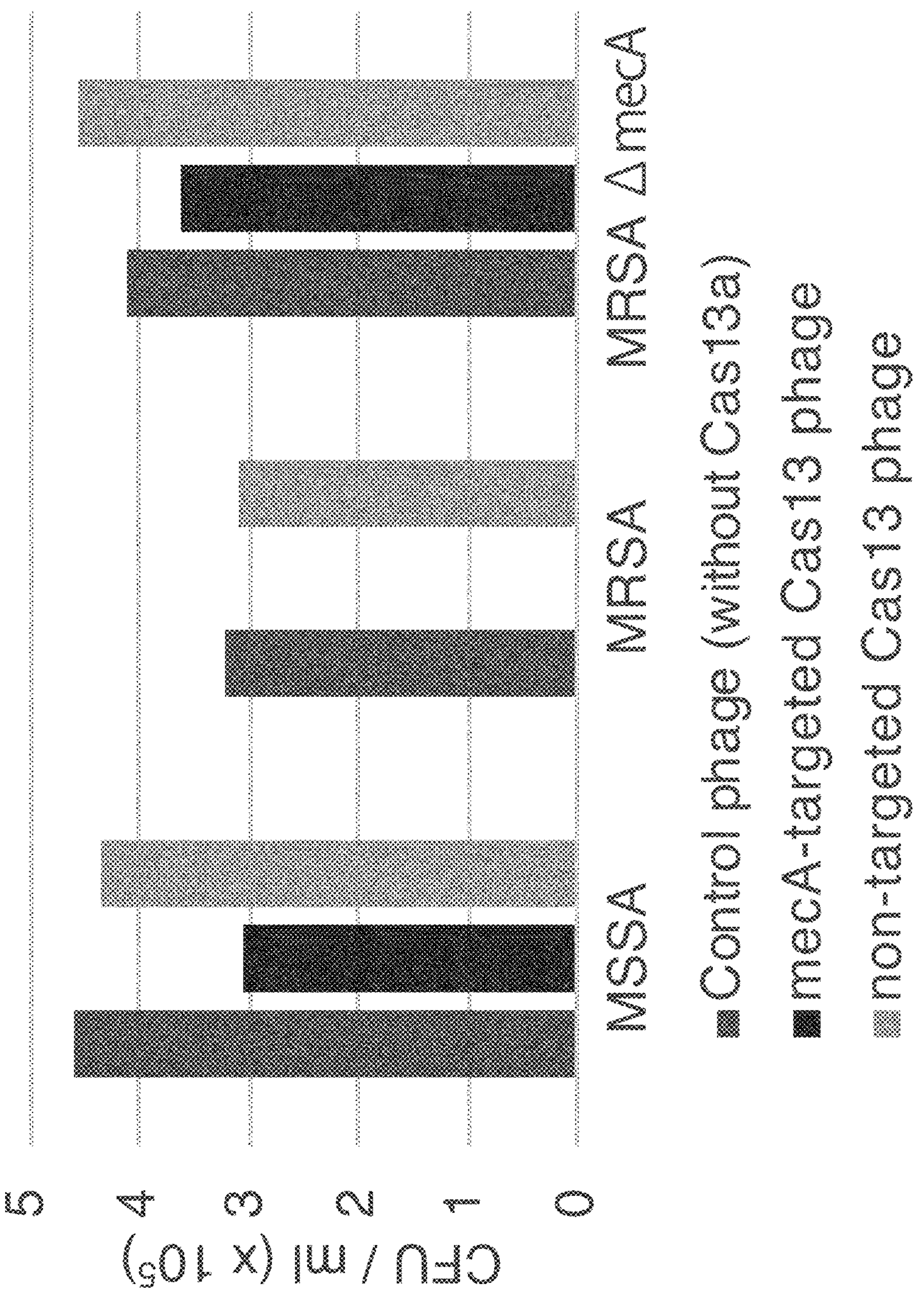
FIG. 19 is a graph showing the results of selective killing of bacteria having the resistance gene mecA of the methicillin-resistant *Staphylococcus aureus* strain according to Example 2 of the present invention and identification of mecA-positive bacteria.

FIG. 19 is a graph of experimental results showing that antibacterial phage prepared for *Staphylococcus aureus* also has a selective bactericidal effect to the *Staphylococcus aureus* having the methicillin resistance gene mecA. The mecA crRNA-446-as, "TATCCCAAAGCATACATATTGAAAATTTAAAAT" and mecA crRNA-446-s, "AAACATTTTAAATTTTCAATATGTATGCTTTGG", which targeted mecA, were synthesized, after annealing, it was inserted into the BsaI site of pKLC21. The packaging sequences were ligated so that the Cas13a crRNA region of pKLC21 BsaI mecA was packaged in phage NM1, and *Staphylococcus aureus* RN4220 where NM1 phage lacking the packaging sequence was in a state of lysogenization was transformed by using it. Then, the transformed RN4220 strain was cultured in TSB medium at 37 degree C., and mitomycin C (2 micro-g/ml) was added when the OD600 reached 0.2. Then, the mixture was shaken at 30 degree C. overnight at 80 rpm to obtain antibacterial phage through a 0.22 micro-m filter. For RN4220 that does not have mecA, clinical isolate USA300 that has mecA, and clinical isolate USA300-delta-mecA that lacks mecA, antibacterial phage targeting mecA was added in the same manner as in FIG. 14, and after culturing at 37 degree C. for 12 hours, the resistance gene mecA was identified.

According to the results of FIG. 19, colony formation was not confirmed by antibacterial phage in USA300 having mecA, whereas colony formation was confirmed from *Staphylococcus aureus* strains (RN4220 and USA300-delta-mecA) not carrying mecA. From the above results, it was confirmed that not only Gram-negative *E. coli* but also Gram-positive *Staphylococcus aureus* can be tested for specific genes by the antibacterial phage.

Incidentally, configuration and operation of the above-mentioned embodiment are just an example, needless to say, it can be appropriately modified and executed without departing from the aim of the present invention.

INDUSTRIAL APPLICABILITY

According to the present invention, antibacterial phage, which bacteria having a drug resistance gene can be selectively sterilized or easily identified, can be provided as a therapeutic composition, bactericidal agent, food, bacterial identification kit, or the like, since these methods are feasible, they are industrially applicable.

The invention claimed is:

1. An antibacterial phage including

CRISPR-Cas13a having a targeting sequence that is complementary to a specific gene as a target and suppressing growth and causing bactericidal action to bacteria, wherein the specific gene is a drug resistance gene, a pathogenic gene, or a toxin gene; and the specific gene is selected from IMP-1, KPC-2, NDM-1, OXA-48, VIM-2, mcr-1, mcr-2, mcr-3, mcr-4, and mcr-5.

2. The antibacterial phage according to claim 1, wherein the target sequence is designed as a spacer sequence for crRNA of 14 to 28 bases.

3. The antibacterial phage according to claim 1, wherein the bactericidal action to bacteria is targeted to any bacteria having the specific gene.

4. The antibacterial phage according to claim 1, wherein the specific gene is having in bacterial genome and/or plasmid for one or any combination of:

Methicillin-Resistant *Staphylococcus aureus* (MRSA), Vancomycin-Resistant *Staphylococcus aureus* (VRSA), Vancomycin-Resistant enterococci (VRE), Penicillin-Resistant *Streptococcus Pneumoniae* (PRSP), Multidrug-resistant *Pseudomonas aeruginosa* (MDRP), Multiple Drug-Resistant *Acinetobacter* (MDRA), carbapenem-resistant *Pseudomonas aeruginosa* (CRPA), carbapenem-resistant *Serratia* (CRSA), third-generation cephalosporin-resistant *pneumoniae* (3GCRKP), third-generation cephalosporin-resistant *E. coli* (3GCREC), fluoroquinolone-resistant *E. coli* (FQREC), and colistin-resistant *E. coli* (ColR-EC).

5. The antibacterial phage according to claim 1, wherein the specific gene is a toxin gene or a pathogenic gene included in a bacterial genome and/or a plasmid of one or any combination of:

*Staphylococcus aureus, Clostridium botulinum, Vibrio cholerae, Escherichia coli, Vibrio parahaemolyticus, Clostridium tetani, Clostridium perfringens, Staphylococcus pyogenes, Clostridium difficile, Bordetella pertussis, Corynebacterium diphtheriae, Shigella dysenteriae, Bacillus anthracis, Pseudomonas aeruginosa, Listeria monocytogenes*, and *Staphylococcus pneumoniae.*

6. The antibacterial phage according to claim 1, wherein the target sequence is a specific 14-28 base sequence of the target gene sequence.

7. An antibacterial phage including

CRISPR-Cas13a having a targeting sequence that is complementary to a specific gene as a target and suppressing growth and causing bactericidal action to bacteria, wherein the specific gene is a drug resistance gene, a pathogenic gene, or a toxin gene; and the target sequence includes:

SEQ ID NO: 7, SEQ ID NO: 17, SEQ ID NO: 22, SEQ ID NO: 26, SEQ ID NO: 27, SEQ ID NO: 28, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, or SEQ ID NO: 52.

8. The antibacterial phage according to claim 1, wherein the specific gene causes drug resistance by nucleic acid acquisition and/or nucleic acid mutation.

9. The antibacterial phage according to claim 1, wherein the target is a plurality of sequences, and each of a plurality of specific genes is recognized as the target.

10. A therapeutic composition including:

the antibacterial phage according to any one of claim 1.

11. A bactericidal agent including:

the antibacterial phage according to any one of claim 1.

12. A food including:

the antibacterial phage according to any one of claim 1.

13. A bacteria identification kit including:

the antibacterial phage according to any one of claim 1.

14. A therapeutic composition manufacturing method comprising the steps of:

transforming and/or infecting a phagemid having a packaging sequence, Cas13a, and CRISPR with a target sequence that recognizes a specific gene as a target, and helper phage with a phage-synthesizing bacteria, and lysing and/or releasing out of the cell; and obtaining constructed antibacterial phage suppressing growth and causing bactericidal action to bacteria;

wherein the specific gene is selected from IMP-1, KPC-2, NDM-1, OXA-48, VIM-2, mcr-1, mcr-2, mcr-3, mcr-4, and mcr-5.

15. A bacteria elimination method comprising the steps of:

applying antibacterial phage including CRISPR-Cas13a having a target sequence that recognizes a specific gene as a target; and eliminating bacteria having the specific gene by causing bactericidal action to the bacteria;

wherein the specific gene is selected from IMP-1, KPC-2, NDM-1, OXA-48, VIM-2, mcr-1, mcr-2, mcr-3, mcr-4, and mcr-5.

16. The bacteria elimination method according to claim 15, wherein the bacteria are present in the flora of humans, animals, and/or an environment.

17. The bacteria elimination method according to claim 15, wherein the bacteria are present in food.

18. A bacteria identification method comprising the steps of:

infecting bacteria with antibacterial phage including CRISPR-Cas13a having a target sequence that recognizes a specific gene as a target; and determining and/or testing whether the bacteria have the specific gene by suppressing growth and causing bactericidal action to the bacteria, wherein the specific gene is a drug resistance gene, a pathogenic gene, or a gene for discriminating the bacteria; and the specific gene is selected from IMP-1, KPC-2, NDM-1, OXA-48, VIM-2, mcr-1, mcr-2, mcr-3, mcr-4, and mcr-5.

19. The bacteria identification method according to claim 18, wherein the antibacterial phage including a sequence of an antibiotic resistance gene.

20. The bacteria identification method according to claim 18, wherein the bacteria are bacteria being present in the bacterial flora in humans, animals, foods, or the environment, and/or genetically modified bacteria.

21. An animal therapeutic method comprising:

applying antibacterial phage including CRISPR-Cas13a having a target sequence that recognizes a specific gene as a target;

treating infectious diseases caused by bacteria having the specific gene in the animal other than a human by suppressing growth and causing bactericidal action to the bacteria;

wherein the specific gene is selected from IMP-1, KPC-2, NDM-1, OXA-48, VIM-2, mcr-1, mcr-2, mcr-3, mcr-4, and mcr-5.

* * * * *